United States Patent [19]

Birnstiel et al.

[11] Patent Number: 5,922,859

[45] Date of Patent: *Jul. 13, 1999

[54] COMPLEXES CONTAINING NUCLEIC ACID WHICH CAN BE TAKEN-UP BY ENDOCYTOSIS INTO HIGHER EUKARYOTIC CELLS

[75] Inventors: Max L. Birnstiel; Matthew Cotten, both of Vienna; Ernst Wagner, Langenzersdorf, all of Austria

[73] Assignees: Boehringer Ingelheim International GmbH, Ingelheim am Rhein, Germany; Genentech, Inc., South San Francisco, Calif.

[*] Notice: This patent is subject to a terminal disclaimer.

[21] Appl. No.: 08/098,265

[22] PCT Filed: Feb. 1, 1992

[86] PCT No.: PCT/EP92/00217

§ 371 Date: Aug. 5, 1993

§ 102(e) Date: Aug. 5, 1993

[87] PCT Pub. No.: WO92/13570

PCT Pub. Date: Aug. 20, 1992

[51] Int. Cl.$^6$ .............................. A61K 48/00; C07H 21/04
[52] U.S. Cl. ........................................ 536/24.5; 435/172.1
[58] Field of Search ...................... 435/8, 172.1; 514/44; 536/24.5; 530/358; 935/52, 54, 55, 56

[56] References Cited

U.S. PATENT DOCUMENTS

| | | | |
|---|---|---|---|
| 5,087,616 | 2/1992 | Myers et al. | 514/21 |
| 5,126,433 | 6/1992 | Maddon et al. | 530/395 |
| 5,166,320 | 11/1992 | Wu et al. | 530/395 |
| 5,169,933 | 12/1992 | Anderson et al. | 530/391.3 |
| 5,192,553 | 3/1993 | Boyse et al. | 530/345 |
| 5,225,182 | 7/1993 | Sharma | 424/9 |
| 5,240,846 | 8/1993 | Collins et al. | 435/240.1 |
| 5,354,844 | 10/1994 | Beug et al. | 530/345 |
| 5,428,132 | 6/1995 | Hirsch et al. | 530/387.1 |

FOREIGN PATENT DOCUMENTS

| | | |
|---|---|---|
| 2012311 | 3/1990 | Canada . |
| WO 90/01951 | 3/1990 | WIPO . |
| WO 92/06180 | 4/1992 | WIPO . |
| WO 92/19749 | 11/1992 | WIPO . |
| WO 92/20316 | 11/1992 | WIPO . |
| WO 92/22635 | 12/1992 | WIPO . |
| WO 93/04701 | 3/1993 | WIPO . |

OTHER PUBLICATIONS

Jung et al., "Biological Activity of the Antitumor Protein Neocarzinostatin coupled to a monoclonal antibody by N–Succinimidyl 3–(2–pyridyldithio)–propionate," *Biochem. & Biophys. Res. Comm.* 101:599–606 (Jul. 30, 1981).
Kaplan & Nielsen, "Analysis of Macrophage Surface Receptors," *J. Biol. Chem.* 254:7323–7328 (Aug. 10, 1979).
Kasid et al., "Human gene transfer: Characterization of human tumor–infiltrating lymphocytes as vehicles for retroviral–mediated gene transfer in man," *Proc. Natl. Acad. Sci. USA* 87:473–477 (Jan. 1990).
Keller et al., "Expression of a foreign gene in myeloid and lymphoid cells derived from multipotent haematopoietic precursors," *Nature* 318:149–154 (Nov. 14, 1985).
Klausner et al., "Binding of apotransferrin to K562 cells: Explanation of the transferrin cycle," *Proc. Natl. Acad. Sci. USA* 80:2263–2266 (Apr. 1983).
Klausner et al., "Receptor–mediated Endocytosis of Transferrin in K562 Cells," *J. Biol. Chem.* 258:4715–4724 (Apr. 25, 1983).
Kuhn & Kraehenbuhl, "The sacrificial receptor–translocation of polymeric IgA across epithelia," *Trends Biochem. Sci.* 7:299–302 (Aug. 1982).
Kurachi & Davie, "Isolation and characterization of a cDNA coding for human factor IX," *Proc. Natl. Acad. Sci. USA* 79:6461–6464 (Nov. 1982).
Laemmli, U.K., "Characterization of DNA condensates induced by poly(ethylene oxide) and polylysine," *Proc. Natl. Acad. Sci. USA* 72:4288–4292 (1975).
Lapidot & Loyter, "Fusion–mediated microinjection of Liposome–enclosed DNA into cultured cells with the aid of influenza virus glycoproteins," *Experimental Cell Res.* 189:241–246 (1990).
Lasky et al., "Neutralization of the AIDS Retrovirus by Antibodies to a Recombinant Envelope Glycoprotein," *Science* 233:209–212 (Jul. 11, 1986).
Lasky et al., "Delineation of a Region of the Human Immunodeficiency Virus Type 1 gp120 Glycoprotein Critical for Interaction with the CD4 Receptor," *Cell* 50:975–985 (1987).
Lim & Chae, "A Simple Assay for DNA Transfection by Incubation of the Cells in Culture Dishes with Substrates for Beta–Galactosidase," *BioTechniques* 7:576–579 (1989).
Lori et al., "Non Retroviral Delivery of Protective Genes Against HIV–1," *Cold Spring Harbor Gene Therapy Conference* (Jul. 1992).
MacGregor & Caskey, "Construction of plasmids that express E.coli β–galactosidase in mammalian cells," *Nucl. Acids Res.* 17:2365 (1989).
Malim et al., "Functional Dissection of the HIV–1 Rev Trans–Activator–Derivation of a Trans–Dominant Repressor of Rev Function," *Cell* 58:205–214 (Jul. 14, 1989).

(List continued on next page.)

*Primary Examiner*—Scott W. Houtteman
*Attorney, Agent, or Firm*—Sterne, Kessler, Goldstein & Fox P.L.L.C.

[57] ABSTRACT

Complexes between internalizing factor-bonding factor conjugates and nucleic acid which can be taken up into higher eukaryotic cells by endocytosis containing, in non-covalently bound form, one or more substances having an affinity for nucleic acid, which are capable of increasing the efficiency of absorption of the complexes into the cells. The non-covalently bound substance having an affinity for nucleic acid may optionally be identical to the bonding factor, preferably a polycationic substance. The internalizing factor is preferably transferrin. Processes for preparing the complexes and processes for introducing nucleic acid into higher eukaryotic cells. Pharmaceutical preparations containing complexes with a therapeutically active nucleic acid.

57 Claims, 14 Drawing Sheets

OTHER PUBLICATIONS

Marsh & Helenius, "Virus Entry into Animal Cells," *Adv. in Virus Res. 36:*107–151 (1989).

Marshall, S., "Kinetics of Insulin Receptor Internalization and Recycling in Adipocytes," *J. Biol. Chem. 260:*4136–4144 (Apr. 10, 1985).

Massague & Kelly, "Internalization of Transforming Growth Factor–β and Its Receptor in BALB/c 3T3 Fibroblasts," *J. Cell. Phys. 128:*216–222 (1986).

McClure et al., "The pH independence of mammalian retrovirus infection," *J. Gen. Virol. 71:*767–773 (1990).

Mellman & Plutner, "Internalization and Degradation of Macrophage Fc Receptors Bound to Polyvalent Immune Complexes," *J. Cell. Biol. 98:*1170–1177 (Apr. 1984).

Mizel et al., "The Interleukin 1 Receptor. Dynamics of Interleukin 1 Binding and Internalization in T Cells and Fibroblasts," *J. Immunol. 138:*2906–2912 (May 1, 1987).

Otero & Carrasco, "Proteins are cointernalized with virion particles during early infection," *Virology 160:*75–80 (1987).

Parente et al., "Mechanism of Leakage of Phospholipid Vesicle Contents Induced by the Peptide GALA," *Biochem. 29:*8720–8728 (1990).

Pelchen–Matthews et al., "Internalization and recycling of CD4 transfected into HeLa and NIH3T3 cells," *EMBO J. 8:*3641–3649 (1989).

Piazza et al., "Attachment of Influenza A Virus to Ferret Tracheal Epithelium at Different Maturational Stages," *Am. J. Resp. Cell Mol. Biol. 4:*82–87 (1991).

Ponder et al., "Mouse hepatocytes migrate to liver parenchyma and function indefinitely after intrasplenic transplantation," *Proc. Natl. Acad. Sci. USA 88:*1217–1221 (Feb. 1991).

Posner et al., "Effect of Colchicine on the Uptake of Prolactin and Insulin into Golgi Fractions of Rat Liver," *J. Cell Biol. 93:*560–567 (Jun. 1982).

Rafalski et al., "Phospholipid Interactions of Synthetic Peptides Representing the N–Terminus of HIV gp41," *Biochem. 29:*7917–7922 (1990).

Riordan et al., "Identification of the Cystic Fibrosis Gene: Cloning and Characterization of Complementary DNA," *Science 245:*1066–1073 (Sep. 8, 1989).

Rosenberg et al., "Immunization of Cancer Patients Using Autologous Cancer Cells Modified by Insertion of the Gene for Interleukin–2," *Human Gene Therapy 3:*75–90 (1992).

Sambrook J., "Expression of Cloned Genes in Cultured Mammalian Cells," *J. Molec. Cloning,* 2nd edition, vol. 3:16.39–16.40 (1989).

Schalch et al., "Interaction of Insulin–Like Growth Factor I/Somatomedin–C with Cultured Rat Chondrocytes: Receptor Binding and Internalization," *Endocr. 118:*1590–1597 (1986).

Sennett & Rosenberg, "Transmembrane Transport of Cobalamin in Prokaryotic and Eukaryotic Cells," *Am. Rev. Biochem. 50:*1053–1086 (1981).

Severne et al., "Metal binding 'finger' structures in the glucocorticoid receptor defined by site–directed mutagenesis," *EMBO J. 7:*2503–2508 (1988).

Shepherd, V., "Intracellular Pathways and mechanisms of sorting in receptor–mediated endocytosis," *TiPs 10:*458–462 (Nov. 1989).

Sly & Fischer, "The Phosphomannosyl Recognition System for Intracellular and Intercellular Transport of Lysosomal Enzymes," *J. Cell. Biochem. 18:*67–85 (1982).

Smith & Cantrell, "Interleukin 2 regulates its own receptors," *Proc. Natl. Acad. Sci. USA 82:*864–868 (Feb. 1985).

Stahl et al., "Evidence for receptor–mediated binding of glycoproteins, glycoconjugates, and lysosomal glycosidases by alveolar macrophages," *Proc. Natl. Acad. Sci. USA 75:*1399–1403 (Mar. 1978).

Strauss & Jaenisch, "Molecular complementation of a collagen mutation in mammalian cells using yeast artificial chromosomes," *EMBO J. 11:*417–422 (1992).

Subbarao et al., "pH–Dependent Bilayer Destabilization by an Amphipathic Peptide," *Biochem. 26:*2964–2972 (1987).

Sullenger et al., "Overexpression of TAR Sequences Renders Cells Resistant to Human Immunodeficiency Virus Replication," *Cell 63:*601–608 (Nov. 2, 1990).

Trono et al., "HIV–1 Gag Mutants Can Dominantly Interfere with the Replication of the Wild–Type Virus," *Cell 59:*113–120 (Oct. 6, 1989).

Uchida et al., "Distribution of Neuraminidase in Arthrobacter and Its Purification by Affinity Chromatography," *J. Biochem. 82:*1425–1433 (1977).

Urakawa et al., "Synthesis of Immunogenic, but Non–infectious, Poliovirus Particles in Insect Cells by a Baculovirus Expression Vector," *J. Gen. Virol. 70:*1453–1463 (1989).

Valerio et al., "Cloning of human adenosine deaminase cDNA and expression in mouse cells," *Gene 31:*147–153 (1984).

Wagner et al., "Transferrin–polycation conjugates as carriers for DNA uptake into cells," *Proc. Natl. Acad. Sci. USA 87:*3410–3414 (May 1990).

Wagner et al., "DNA–Binding Transferrin Conjugates as Functional Gene–Delivery Agents: Synthesis by Linkage of Polylysine or Ethidium Homodimer to the Transferrin Carbohydrate Moiety," *Bioconjugate Chem. 2:*226–231 (1991).

Wagner et al., "Transferrin–polycation–DNA complexes: The effect of polycations on the structure of the complex and DNA delivery to cells," *Proc. Natl. Acad. Sci. USA 88:*4255–4259 (May 1991).

Walker et al., "Long–term culture and fine specificity of human cytotoxic T–lymphocyte clones reactive with human immunodeficiency virus type 1," *Proc. Natl. Acad. Sci. USA 86:*9514–9518 (Dec. 1989).

Walker & Burgess, "Internalisation and Recycling of the Granulocyte–Macrophage Colony–Stimulating Factor (GM–CSF) Receptor on a Murine Myelomonocytic Leukemia," *J. Cell. Phys. 130:*255–261 (1987).

Wharton et al., "Membrane Fusion by Peptide Analogues of Influenza Virus Haemagglutinin," *J. Gen. Virol. 69:*1847–1857 (1988).

Wienhues et al., "A Novel Method for Transfection and Expression of Reconstituted DNA–protein Complexes in Eukaryotic Cells," *DNA 6:*81–89 (1987).

Wilchek & Bayer, "The Avidin–Biotin Complex in Bioanalytical Applications," *Analyt. Biochem. 171:*1–32 (1988).

Willumsen et al., "Intracellular Cl⁻ activity and cellular Cl⁻ pathways in cultured human airway epithelium," *Am. J. Physiol. 256:*C1033–C1044 (1989).

Wood et al., "Expression of active human factor VIII from recombinant DNA clones," *Nature 312:*330–337 (Nov. 22, 1984).

Wu & Wu, "Receptor–mediated in Vitro Gene Transformation by a Soluble DNA Carrier System," *J. Biol. Chem. 262:*4429–4432 (Apr. 5, 1987).

Wu & Wu, "Evidence for Targeted Gene Delivery to Hep G2 Hepatoma Cells in Vitro," *Biochemistry 27:*887–892 (1988).

Wu & Wu, "Receptor–mediated Gene Delivery and Expression in Vivo," *J. Biol. Chem. 263:*14621–14624 (Oct. 15, 1988).

Yankaskas et al., "E6 and E7 Genes of Human Papilloma Virus 18 (HPV 18) Transform Human Airway Epithelial Cells," *Genetics and Epithelial Cell Dysfunctions in Cystic Fibrosis,* Alan R. Liss, Inc., A139 (1991).

Zamecnik et al., "Inhibition of replication and expression of human T–cell lymphotropic virus type III in cultured cells by exogenous synthetic oligonucleotides complementary to viral RNA," *Proc. Natl. Acad. Sci. USA 83:*4143–4146 (Jun. 1986).

Zatloukal et al., "Hepatocellular Cytokeratins as Substrates of Transglutaminases," *Lab. Investig. 61:* 603–608 (1989).

Zatloukal et al., "Transferrinfection: receptor–mediated gene delivery in vitro and in vivo," *Cold Spring Harbor Gene Therapy Conference* (Jul. 1992).

Zenke et al., "Receptor–mediated endocytosis of transferrin–polycation conjugates: An efficient way to introduce DNA into hematopoietic cells," *Proc. Natl. Acad Sci. USA 87:*3655–3659 (May 1990).

Morin, J.E., et al., "Recombinant Adenovirus Induces Antibody Response to Hepatitis B Virus Surface Antigen in Hamsters," *Proc. Natl. Acad. Sci. USA 84:*4626–4630 (1987).

Abrahamson & Rodewald, "Evidence for the Sorting of Endocytic Vesicle Contents during the Receptor–mediated Transport of IgG across the Newborn Rat Intestine," *J. Cell Biol. 91:*270–280 (Oct. 1981).

American Type Culture Collection, "Catalogue of Animal Viruses and Antisera, Chlamydiae and Rickettsiae," edited by Buck, C. & Paulino, G., Sixth Edition pp. 1–17 (1990).

Anderson et al., "Specific Binding of $^{125}$I–Human Interferon–γ to High Affinity Receptors on Human Fibroblasts," *J. Biol. Chem. 257:*11301–11304 (Oct. 10, 1982).

Ansardi et al., "Coinfection with Recombinant Vaccinia Viruses Expressing Poliovirus P1 and P3 Proteins Results in Polyprotein Processing and Formation of Empty Capsid Structures," *J. Virol. 65:*2088–2092 (Apr. 1991).

Armentano et al., "Effect of Internal Viral Sequences on the Utility of Retroviral Vectors," *J. Virol. 61:*1647–1650 (May 1987).

Armentano et al., "Expression of human factor IX in rabbit hepatocytes by retrovirus–mediated gene transfer: Potential for gene therapy of hemophilia B," *Proc. Natl. Acad. Sci. USA 87:*6141–6145 (Aug. 1990).

Asada–Kubota et al., "Binding and internalization of $^{125}$I–glucagon in hepatocytes of intact mouse liver. An autoradiographic study," *Exp. Path. 23:*95–101 (1983).

Ascoli & Puett, "Inhibition of the Degradation of Receptor-–bound Human Choriogonadotropin by Lysosomotropic Agents, Protease Inhibitors, and Metabolic Inhibitors," *J. Biol. Chem. 253:*7832–7838 (Nov. 10, 1978).

Ashwell & Harford, "Carbohydrate–Specific Receptors of the Liver," *Ann. Rev. Biochem. 51:*531–554 (1982).

Barr & Leiden, "Systemic Delivery of Recombinant Proteins by Genetically Modified Myoblasts," *Science 254:*1507–1509 (Dec. 6, 1991).

Baum & Paulson, "Sialyloligosaccharides of the respiratory epithelium in the selection of human influenza virus receptor specificity," *Acta Histochem. Suppl. 40:*35–38 (1990).

Berns, K., "Parvoviridae and their Replication," *Virology,* 2nd edition, edited by Fields, B.N., Knipe, D.M. et al., Raven Press Ltd., NY, pp. 1743–1763 (1990).

Carpenter, G., "Properties of the Receptor for Epidermal Growth Factor," *Cell 38:*357–358 (Jun. 1984).

Cheng et al., "Receptor–mediated uptake of 3,3',5–tri-iodo–L–thyronine by cultured fibroblasts," *Proc. Natl. Acad. Sci. USA 77:*3425–3429 (Jun. 1980).

Ciliberto et al., "Cell–Specific Expression of a Transfected Human $α_1$–Antitrypsin Gene," *Cell 41:*531–540 (Jun. 1985).

Clarke, D.D. et al., "The Incorporation of Amines into Protein," *Arch. Biochem. & Biophys. 79:*338–354 (1959).

Clarke, L.L. et al., "Defective Epithelial Chloride Transport in a Gene–Targeted Mouse Model of Cystic Fibrosis," *Science 257:*1125–1128 (Aug. 21, 1992).

Collis et al., "Definition of the minimal requirements within the human β–globin gene and the dominant control region for high level expression," *EMBO J. 9:*233–240 (1990).

Cotten et al., "High–efficiency receptor–mediated delivery of small and large (48 kilobase gene constructs using the endosome–disruption activity of defective or chemically inactivated adenovirus particles," *Proc. Natl. Acad. Sci. USA 89:*6094–6098 (Jul. 1992).

Curiel D. et al., "Gene Transfer to Respiratory Epithelial Cells via the Receptor–mediated Endocytosis Pathway," *Am. J. Resp. Cell Mol. Biol. 6:*247–252 (1992).

Curiel, D. et al., "In vivo gene transfer to airway epithelium employing molecular conjugate vectors," *Cold Spring Harbor Gene Therapy Conference* (Jul. 1992).

Curiel, T. et al., "Foreign Gene Expression in EBV–Transformed B–Cells: Potential for the Development of Novel CTL Target Cells," *J. Cell. Biochem. Suppl. 60:*Q407 (1992).

Davidson & Hassell, "Overproduction of Polyomavirus Middle T Antigen in Mammalian Cells through the Use of an Adenovirus Vector," *J. Virol. 61:*1226–1239 (Apr. 1987).

De Wet et al., "Firefly Luciferase Gene: Structure and Expression in Mammalian Cells," *Mol. & Biol. 7:*725–738 (Feb. 1987).

Dhawan et al., "Systemic Delivery of Human Growth Hormone by Injection of Genetically Engineered Myoblasts," *Science 254:*1509–1512 (Dec. 6, 1991).

Eaton et al., "Construction and Characterization of an Active Factor VIII Variant Lacking the Central One–Third of the Molecule," *Biochem. 25:*8343–8347 (Dec. 30, 1986).

Farber et al., "Optimal Conditions for Uptake of Exogenous DNA by Chinese Hamster Lung Cells Deficient in Hypoxanthine–Guanine phosphoribosyltransferase," *Biochim. et Biophys. Acta 390:*298–311 (1975).

Fernandez–Puentes & Carrasco, "Viral Infection Permeabilizes Mammalian Cells to Protein Toxins," *Cell 20:*769–775 (Jul. 1980).

FitzGerald et al.,"Adenovirus–Induced Release of Epidermal Growth Factor and Pseudomonas Toxin into the Cytosol of KB Cells during Receptor–Mediated Endocytosis," *Cell 32:*607–617 (Feb. 1983).

Folk & Chung, "Transglutaminases," *Methods in Enzym. 113:*358–385 (1985).

Fujiwara et al., "Novel Preparation Method of Immunogen for Hydrophobic Hapten, Enzyme Immunoassay for Daunomycin and Adriamycin," *J. Immunol. Meth. 45:*195–203 (1981).

Ginsberg et al., "Picornaviruses," *Microbiology,* 3rd Edition, edited by Davis, B.D. et al., Harper & Row, pp. 1095–1117 (1980).

Goldstein et al., "Binding site on macrophages that mediates uptake and degradation of acetylated low density lipoprotein, producing massive cholesterol deposition," *Proc. Natl. Acad. Sci. USA 76:*333–338 (Jan. 1979).

Goldstein et al., "What should be called a lectin?," *Nature 285:*66 (May 8, 1980).

Goldstein & Brown, "Lipoprotein Receptors: Genetic Defense Against Atherosclerosis," *Clin. Res. 30:*417–426 (1982).

Green et al., "Mutational Analysis of HIV–1 Tat Minimal Domain Peptides: Identification of Trans–Dominant Mutants that Suppress HIV–LTR–Driven Gene Expression," *Cell 58:*215–223 (Jul. 14, 1989).

Harris et al., "Gene Transfer to Primary Airway Epithelial Cells Employing Molecular Conjugate vectors," *Clinical Research Abstracts 40:*317A (Apr. 1992).

Hearst & Thiry, "The photoinactivation of an RNA animal virus, vesicular stomatitis virus, with the aid of newly synthesized psoralen derivatives," *Nucl. Acids Res. 4:*1339–1347 (1977).

Heldin et al., "Interaction of a platelet–derived growth factor with its fibroblast receptor," *J. Biol. Chem. 257:*4216–4221 (Apr. 25, 1982).

Helenius et al., "Viruses as Tools in Drug Delivery," *Annals NY Acad. Sci. 507:* 1–6 (1987).

Hirsch et al., "Integration of foreign DNA into cells—by conjugating foreign DNA with target specific antibody and binding to cells," *Derwent Abstract:*C89–126505 (1989).

Hizuka et al., "Polypeptide Hormone Degradation and Receptor Regulation are Coupled to Ligand Internalization," *J. Biol. Chem. 256:*4591–4597 (May 10, 1981).

Holland, J., "Defective Viral Genomes," *Virology,* 2nd Ed., edited by Fields, B.N., Knipe, D.M. et al., Raven Press Ltd., NY, pp. 151–165 (1990).

Hosang & Shooter, "The internalization of nerve growth factor by high–affinity receptors on pheochromocytoma PC12 cells," *EMBO J. 6:*1197–1202 (1987).

Huang, A., "The Role of Defective Interfering (DI) Particles in Viral Infection," *The Molecular Basis of Viral Replication,* edited by Bercoff, R.P., Plenum Press, NY & London, pp. 191–194 (1987).

Imamura et al., "Expression of Tumor Necrosis Factor Receptors on Human Monocytes and Internalization of Receptor Bound Ligand," *J. Immunology 139:*2989–2992 (Nov. 1, 1987).

Iwanij, V., "The Use of Liver Transglutaminase for Protein Labeling," *Eur. J. Biochem. 80:*359–368 (1977).

Jacobs et al., "Binding Sites of Attachment–Inhibiting Monoclonal Antibodies and Antibodies from Patients on Peptide Fragments of the *Mycoplasma pneumoniae* Adhesin," *Infection & Immunity 57:*685–688 (Mar. 1989).

Brown, Washington Post Dec. 8, 1996, p. 1, p. A22, col. 1.

Stein et al., Science, 261:1004–1012, Aug. 20, 1993.

Cotten et al., Proc. Natl. Acad. Sci. 87:4033–4037, Jun. 1990.

ManFioletti et al., Nucleic Acids Res., 19(24), 6793–7.

COMPLEXES CONTAINING NUCLEIC ACID WHICH CAN BE TAKEN-UP BY ENDOCYTOSIS INTO HIGHER EUKARYOTIC CELLS

This application is the national filing of international application PCT/EP92/00217, filed Feb. 1, 1992.

FIELD OF THE INVENTION

The invention relates to the introduction of nucleic acids by endocytosis into higher eukaryotic cells by means of internalizing factors.

BACKGROUND OF THE INVENTION

In recent years, nucleic acids have acquired greater significance as therapeutically active substances, e.g. antisense RNAs and DNAs have proved to be effective agents for selectively inhibiting certain genetic sequences. Their mode of activity enables them to be used as therapeutic agents for blocking the expression of certain genes (such as deregulated oncogenes or viral genes) in vivo. It has already been shown that short antisense oligonucleotides can be imported into cells and perform their inhibiting activity therein (Zamecnik et al., 1986), even though the intracellular concentration thereof is low, partly because of their restricted uptake through the cell membrane owing to the strong negative charge of the nucleic acids.

Another method of selectively inhibiting genes consists in the application of ribozymes. Here again there is the need to guarantee the highest possible concentration of active ribozymes in the cell, for which transportation into the cell is one of the limiting factors.

There is also a need for an efficient system for introducing nucleic acid into living cells in gene therapy. For this, genes are delivered into cells in order to achieve the synthesis of therapeutically active gene products in vivo.

Increasingly, there is a need for methods of treatment in which the therapeutically active DNA (or mRNA) is administered like a drug ("gene therapeutic agent") either once or repeatedly, as required. Examples of genetically caused diseases in which gene therapy constitutes a promising approach are hemophilia, betathalassemia and "Severe Combined Immune Deficiency" (SCID), a syndrome caused by a genetically induced lack of the enzyme adenosine deaminase. Other possible applications are in immune regulation in which a humoral or intracellular immunity is achieved by the administration of functional nucleic acid which codes for a secreted protein antigen or for a non-secreted protein antigen, by means of an inoculation. Other examples of genetic defects in which a nucleic acid coding for the defective gene can be administered, e.g. in a form tailored to the individual requirements, include muscular dystrophy (dystrophin gene), cystic fibrosis ("Cystic fibrosis transmembrane conductance regulator gene") and hypercholesterolemia (LDL receptor gene). Methods of treatment by gene therapy are also of potential significance where hormones, growth factors or proteins with a cytotoxic or immunomodulating activity are to be synthesized in the body.

Numerous solutions have already been proposed for improving the transportation of nucleic acids into living cells, which is one of the limiting factors in the therapeutic use thereof.

One of these possible solutions consists of directly modifying the nucleic acids, e.g. by substituting the charged phosphodiester groups with uncharged groups. Another possible method of direct modification consists in using nucleoside analogues. However, these proposals have various disadvantages, e.g. reduced binding to the target molecule, a poorer inhibitory effect and possible toxicity.

An alternative approach to the direct modification of the oligonucleotides consists in leaving the oligonucleotide per se unchanged and providing it with a group which gives it the desired properties, e.g. with molecules which facilitate transportation into the cells.

There are various known techniques for the genetic transformation of mammalian cells in vitro, but their use in vivo is restricted (they include the introduction of DNA by means of viruses, liposomes, electroporation, microinjection, cell fusion, DEAE-dextran or the calcium phosphate precipitation method).

Attempts have already been made to develop a soluble system which can be used in vivo to convey the DNA into the cells in targeted manner (Wu and Wu, 1987). This system was developed for hepatocytes and is based on the principle of coupling polylysine to a glycoprotein to which a receptor provided on the hepatocyte surface responds and then, by adding DNA, forming a soluble glycoprotein/polylysine/DNA complex which is taken up into the cell and, once taken up, allows the DNA sequence to be expressed.

This system is specific to hepatocytes and is defined, in terms of its function, by a relatively well characterized absorption mechanism involving the asialoglycoprotein receptor.

A broadly applicable and efficient transport system makes use of the transferrin receptor for taken up nucleic acids into the cell by means of transferrin-polycation conjugates. This system is the subject of EP-A1 0388 758, the contents of which are hereby referred to.

It has been shown that DNA transported into the cell by means of this system is expressed and that, if nucleic acid with an inhibiting effect is used, the inhibiting effect is not impaired by the transporting system. This system will hereinafter be referred to by the name "transferrinfection".

International Patent Application WO 91/17773 relates to a system for transporting nucleic acids with a specific effect for CD4-expressing cells. This system makes use of the receptor used by the HIV virus, by complexing the nucleic acid which is to be imported with a protein/polycation conjugate, the protein portion of which is a protein with the ability to bind to CD4, and bringing CD4-expressing cells into contact with the protein-polycation/nucleic acid complexes obtained. It has been demonstrated that DNA transported into the cell by means of this system (hereinafter referred to as CD4 transfection) is expressed in the cell.

What is common to both these inventions is the feature that they make use of specific cell functions to enable or facilitate the introduction of nucleic acid into the cell. In both cases, the absorption mechanisms proceed with the involvement of factors which are referred to for the purposes of the invention, as "internalizing factors". This means factors which bind to the cell surface and are internalized cell-type specifically, in the wider or narrower sense, possibly with the cooperation of other factors (e.g. cell surface proteins), and their internalization may be reversible or irreversible. The internalizing factor is conjugated with a substance of a polycationic nature which, because of its affinity for nucleic acids, establishes a connection between itself and the nucleic acid. (Substances with the ability to form a bond between nucleic acid and the internalizing factor are hereinafter referred to as "bonding factor".)

In the course of the two inventions which preceded the present invention it was found that the optimum introduction of nucleic acid into the cell could be achieved if the ratio of conjugate to nucleic acid was selected to be such that the internalizing factor-polycation/nucleic acid complexes were substantially electroneutral.

SUMMARY OF THE INVENTION

The present invention is directed to a complex which can be taken up by endocytosis into higher eukaryotic cells by means of an internalizing factor, this complex contains a nucleic acid and an internalizing factor/bonding factor conjugate. The complex is characterized by additionally containing one or more non-covalently bound substances having an affinity for nucleic acid such that the internalization and/or expression of the nucleic acid achieved by the conjugate is increased. The non-covalently bound substance having high affinity for nucleic acid is optionally capable of condensing the nucleic acid.

The present invention is also directed toward a method for preparing complexes for the transfer of nucleic acid into higher eukaryotic cells by mixing the nucleic acid to be transferred with an internalizing factor/bonding factor conjugate and with the non-covalently bound substance having high affinity for the nucleic acid.

The invention is directed to a process for introducing nucleic acid into higher eukaryotic cells by which a complex of the invention is brought into contact with the cells and taken up by the process of endocytosis.

The present invention also relates to a pharmaceutical preparation containing a complex of the invention with a therapeutically effective nucleic acid.

DETAILED DESCRIPTION OF THE PREFERRED EMBODIMENTS

The aim of the present invention was to improve the efficiency of systems in which nucleic acids are taken up by means of internalizing factors.

To solve this problem the composition of those internalizing factor-polycation-nucleic acid complexes which gave the best results in terms of uptake efficiency was investigated in detail in order to make use of the findings to optimize the system.

First, various transferrin-polycation conjugates were synthesized (apart from the isolation step, substantially according to the procedure described in EP-A 1 0388 758). Each conjugate was first tested by titration in preliminary trials to discover its capacity to import a gene (in this case the luciferase reporter gene) into living cells. It was found out that each conjugate/DNA complex had a clear optimum in terms of the ratio of conjugate to DNA. It was observed that transferrin-polylysine conjugates (TfpL) with a high polylysine content showed markedly better results in the transportation of DNA than conjugates with a lower polylysine content. Polylysine 450 (pL 450) gave comparable results to polylysine 200 (pL 200), but beyond a certain pL-content of the conjugates (Tf/pL 1/1) the activity decreased again. The best results were obtained with about 100 to 200 positively charged amino acids per transferrin in the conjugate.

Another series of tests were carried out on the principle of using a sub-optimum quantity of the particular conjugate, once the optimum ratio of conjugate to DNA was known, mixing the conjugate with increasing amounts of free (not covalently bound) polycation or a substance of polycationic nature (polylysines of various levels of polymerization and protamines and the histones H1, H3 and H4 were used), and adding the resulting mixture to a constant amount of DNA. The transfection efficiency of the complexes, which was significantly below the optimum transfection level when the sub-optimum quantity of conjugate was used, could be fully restored or even exceeded by the addition of free polycation. Only spermidine and spermine, which were known to condense DNA only at a low ionic strength (Tikchonenko et al., 1988) were unable to increase the expression of DNA under the physiological conditions for the tissue culture system.

In the course of the experiments carried out for the purposes of the present invention, a series of transferrin-protamine conjugates was also prepared and investigated for their ability to transport nucleic acid into living cells, using either authentic or synthetic protamines. The conjugates tested did indeed have the ability to transport DNA into the cells but their efficiency was only about one tenth of the efficiency of the polylysine conjugates. With the help of free polylysine the efficiency of the protamine conjugates could be increased substantially.

Similar results were found for the CD4 transfection system. Experiments were carried out with a gp120-polylysine/DNA complex, starting from gp120-polylysine conjugates which had shown relatively poor results at a conjugate/DNA ratio of 2:1. The addition of free polylysine resulted in a four-fold increase in the expression of the imported foreign gene in CD4-expressing Hela cells.

The results obtained led to the assumption that the polycationic binding factor contained in the conjugate, in addition to having the function of establishing the bond between nucleic acid and transferrin, plays an additional role in the uptaken of the nucleic acid into the cell or during expression.

Following the titration experiments to determine the optimum ratios of transferrin to polycation, investigations were carried out on the molecular state of the complexes which were formed under conditions of optimum DNA/conjugate ratios. The aim of these investigations was to examine whether the change in the conjugation ratios affected the higher order structure of the complexes. For this purpose, transferrin-polycation-plasmid-DNA complexes, prepared analogously to the method used for transferrinfection, were examined under the electron microscope. The electron microscopic analysis surprisingly showed that the plasmid DNA in the presence of the conjugates appears compressed into toroidal structures (like doughnuts) with a diameter of about 80 to 100 nm, irrespective of the method of preparation for electron microscopy. The surprising feature of these results was that the doughnut structures, obtained with those conjugates which had proved most efficient in the transferrinfection, conformed to the structure of complexes between DNA and free polylysine, i.e. the ability of polylysine to condense DNA had not been affected by the fact that it was coupled to an internalizing factor. The condensation of λ-DNA by polylysine at high salt concentrations (Laemmli, 1975) or by spermidine at a very low ion intensity (Chattoraj et al., 1978) was known from the literature.

In the course of the experiments it was also found that the increase in expression achieved by non-covalently bound bonding factor in some cases could clearly not be attributed to the condensing effect thereof, or not exclusively to this effect, but must be due to other mechanisms. This was found in the case of histone H4, which brought about a remarkable increase in the efficiency of transferrinfection, without any compacting of the DNA attributable to H4 being observed under the electron microscope.

From the results of the tests carried out it was first inferred that at least two preconditions are necessary for the efficiency of the introduction of the internalizing factor-bonding factor/nucleic acid complexes:

a) the presence of a sufficient quantity of suitable bonding factor in the mixture to ensure that the nucleic acid molecule is bound in a form which is not only compatible with the internalizing and expression thereof but even clearly facilitates these processes. Improved internalizing may possibly, e.g. in the case of transferrin and free polycations which cause compacting of the DNA, be attributed to the fact that the diameter of the condensed "doughnuts" coincides with the dimension of the "coated pits" through which the transferrin bound to its receptor is internalized, the inner diameter of which is about 100 nm (Darnell et al., 1989). (The condensing of the nucleic acid possibly brings about protection from enzymatic degradation, in addition to the easier internalizing.)

b) The presence of internalizing factor in a form and a quantity to maintain the transportation of the complexes (e.g. in the case of transferrin by receptor-mediated endocytosis) into the cell, the high number of internalizing factor molecules per "doughnut" which is obtained when using conjugates with an optimum ratio of conjugate to DNA, apparently not being necessary in order to achieve efficient uptake of the complexes into the cells.

The results of the tests carried out have led to the assumption that the increase in expression brought about by the free bonding factor obviously cannot be attributed, or at least not exclusively, to DNA compacting, but possibly, in addition, to a protective action for the DNA and hence an inhibition of DNA breakdown in the cell and/or a positive influence on the exposure of the nucleic acid to the machinery of expression.

The invention thus starts from the observation that if internalizing factor/polycation conjugates are used, some, of the conjugates may be replaced by non-covalently bound polycations (or substances of a polycationic nature), provided that, after some of the conjugates have been replaced by free nucleic acid-binding substance, there is still a sufficient quantity of conjugate remaining and in a suitable form to ensure the functioning of the uptake mechanism mediated by the internalizing factor.

The experiments carried out within the scope of the present invention using transferrin/polycation conjugates and plasmid DNA have shown that 10 to 20 transferrin molecules are required per molecule of DNA to maintain the transport of genes into the cells. If the number fell below this revel, as a result of the replacement of the conjugates by free polycations, the quantity of imported DNA was dramatically reduced, to levels which are typical of pure cationic importing systems (Farber et al., 1975).

Without wishing to be tied to this theory, it might be crucial, e.g. in the case of transferrin, that the transferrin molecules are not only present in a sufficient or optimum number but that these molecules are also accessible for the receptor, i.e. they are suitably presented to the receptor in order to ensure that the receptor-mediated endocytosis takes place.

It has been found, surprisingly, that the quantity of nucleic acid taken up into the cell is not reduced if some of the transferrin-polycation conjugate is replaced by non-covalently bound polycation; in some cases there may even be a significant increase in the DNA uptake. The tests carried out with CD4 binding proteins as internalizing factor gave similar results.

Hereinafter, the substances contained in the complexes in non-covalently bound form which are able to increase the efficiency of the internalization and/or expression achieved by the conjugates by their ability to bind nucleic acids will be referred to as "nucleic acid-binding substances" or "substances having an affinity for nucleic acid".

It has also been found that the addition of free substances having an affinity for nucleic acid brings about an increase in the efficiency of the importing system even when other bonding factors are used.

Tests to this effect were carried out with the intercalating agent ethidium dimer as the bonding factor, using transferrin-ethidium dimer conjugates. In this system, too, there was also an increase in the expression of the DNA introduced into the cells by means of the conjugates if the DNA/conjugate complexes contained free polycation.

The invention thus relates to new complexes which can be taken up into higher eukaryotic cells by means of internalizing factor by endocytosis, these complexes containing nucleic acid complexed with an internalizing factor/bonding factor conjugate. The complexes are characterised in that they addition ally contain one or more substances having an affinity for nucleic acid, which may possibly be identical to the bonding factor, in a non-covalently bound form such that the internalizing and/or expression of the nucleic acid achieved by the conjugate is increased.

According to another aspect, the invention relates to a process for introducing nucleic acid into higher eukaryotic cells by means of internalizing factors, in which the cells are brought into contact with the complexes according to the invention.

With the aid of the present invention, a smaller quantity, based on the quantity of nucleic acid to be introduced into the cell, of internalizing factor/bonding factor conjugate is required, while the efficiency of transfection/expression remains at least the same, resulting in a reduction in the costs of synthesis. A smaller amount of conjugate may, on the other hand, be advantageous if one wishes to avoid the effect of having several adjacent "docking sites" (e.g. receptors) occupied by a larger number of internalizing factor molecules within a complex, so that these docking sites are consequently no longer available for other complexes. Keeping the quantity of internalizing factor contained in the complexes to the necessary minimum, i.e. minimizing the quantity of conjugate and diluting it with substance having an affinity for free nucleic acid is particularly beneficial if there are not many receptors on the target cells to be treated.

With the aid of the present invention, the performance of conjugates which are not particularly efficient per se can be increased substantially and the performance of conjugates which are already highly efficient can be further increased.

With regard to the qualitative composition of the complexes according to the invention, first of all the nucleic acid to be imported into the cell and the internalizing factor are generally determined. The nucleic acid is defined primarily by the biological effect to be achieved in the cell, e.g. by the target sequence of the gene or gene section to be inhibited or (when used in gene therapy) to be expressed, e.g. In order to substitute a defective gene. The nucleic acid may optionally be modified, e.g. because of the need for stability for the particular application. The nucleic acids to be transported into the cells may be DNAs or RNAs, with no restrictions on the nucleotide sequence. Modifications may exist, for example, in the substitution of the phosphodiester group by phosphorothioates or in the use of nucleoside analogues (Zon, 1988). The therapeutically effective inhibiting nucleic acids which are of particular interest are those which are to be transported into the cell for the purpose of inhibiting specific gene sequences. They include antisense oligonucleotides and ribozymes, optionally together with a carrier nucleic acid (or gene constructs by which antisense RNA or ribozymes are transcribed).

The internalizing factor is foremost defined by the target cells, e.g. by certain surface antigens or receptors which are specific to a type of cell and thus permit a targeted import of nucleic acid into this type of cell.

Starting from the decision as to the nucleic acid and internalizing factor, the bonding factor is matched to these parameters, the size of the nucleic acid, particularly with respect to substantial neutralization of the negative charges, being of particular interest.

When choosing the non-covalently bound substances having an affinity for nucleic acid which are contained in the complexes, it is crucial that the addition of these substances should bring about an increase in the internalization/ expression of the nucleic acid, compared with that which can be achieved by means of the conjugates.

Like the qualitative composition, the quantitative composition of the complexes is also determined by numerous criteria which are functionally connected with one another, e.g. whether and to what extent it is necessary or desirable to condense the nucleic acid, what charge the total complex should have, to what extent the particular type of cell has a binding and internalizing capacity and to what extent it is desirable or necessary to increase it. Other parameters for the composition of the complex are the accessibility of the internalizing factor for the receptor, the crucial factor being the way in which the latter is presented within the complex relative to the cell. Another essential feature is the accessibility of the nucleic acid in the cell in order to perform its designated function.

The term "internalizing factor" for the purposes of the present invention refers t o ligands or fragments thereof which, after binding to the cell by endocytosis, preferably receptor-mediated endocytosis, are internalized, or factors which are bound/internalized by fusion with cell membrane elements.

The theoretically suitable internalizing factors include the ligands transferrin, conalbumin; asialoglycoproteins (such as asialotransferrin, asialorosomucoid or asialofetuin) or substances which contain galactose and are internalized via the asialoglycoprotein receptor; lipoproteins which are taken up into the cell via receptors (apo B100/LDL); viral proteins such as the HIV protein gp120; antibodies against surface antigens, e.g. anti-CD4, anti-CD7; cytokines such as interleukin-1, TNF; factors and growth factors such as insulin, EGF; deactivated toxins. The ligands may be of natural or synthetic origin and may optionally be modified.

For such factors to be suitable within the scope of the present invention
  a) they must be capable of being internalized by the specific cell type into which the nucleic acid is to be introduced and their ability to be internalized should not, or not substantially, be affected if they are conjugated with the bonding factor, and
  b) within t he scope of this property they must be capable of carrying nucleic acid into the cell "piggy-back" by the route which they use.

Bonding factors which are suitable according to the invention include, for example, homologous polycations such as polylysine, polyarginine, polyornithine or heterologous polycations having two or more different positively charged amino acids, these polycations possibly having different chain lengths, as well as non-peptide synthetic polycations such as polyethyleneimine. Other suitable bonding factors are natural DNA-binding proteins of a polycationic nature such as histones or protamines or analogues or fragments thereof. Other bonding factors which may be used are intercalating substances such as ethidium dimers, acridine or intercalating peptides, containing tryptophan and/or tyrosine and/or phenylalanine.

The nucleic acid-binding substances contained in non-covalently bound form in the complexes may be the same as or different from the bonding factors. An essential criterion for selecting them is the size of the nucleic acid, particularly with respect to the condensation thereof; with smaller nucleic acid molecules, compacting is not generally required. The choice of the substances having an affinity for nucleic acid, in terms of the nature and quantity thereof, is also made in accordance with the conjugate, particular account being taken of the bonding factor contained in the conjugate: if for example the bonding factor is a substance which has no or very little capacity for DNA condensation, it is generally advisable, for the purpose of achieving efficient internalizing of the complexes, to use those substances having an affinity for DNA which possess this quality to a greater extent. If the bonding factor itself is a substance which condenses nucleic acid and if adequate compacting of the nucleic acid for efficient internalization is achieved by means of this bonding factor, it is advisable to use a substance having an affinity for nucleic acid which brings about an increase in expression by other mechanisms.

The non-covalently bound substances with an affinity for nucleic acid which are suitable for use according to the present invention include compounds having the ability to condense nucleic acid and/or to protect it from undesirable breakdown in the cells, especially the substances of a polycationic nature mentioned hereinbefore. Another group of suitable substances consists of those which bring about an improvement in the transcription/expression of a nucleic acid by binding to it, thereby improving the accessibility of the nucleic acid for the expression machinery of the cells. An example of such a substance is the chromosomal non-histone protein HMGI, which has been found to have the ability to compact DNA and to express it in the cells, the assumption being that the DNA is activated for transcription (Böttger et al., 1988).

The bonding factors and/or the non-covalently bound substances having an affinity for nucleic acid may optionally be modified. The modification may consist of lipophilic groupings, e.g. hydrocarbon groupings having a similarity to natural lipids (e.g. fatty acids, cholesterol) which are capable of increasing the affinity of the internalizing factor/bonding factor/nucleic acid complexes for the cell membrane.

Another possible method of achieving modification consists in the use of hydrophilic groupings which are capable of increasing the specificity of the complexes for the target cells, these groupings preventing the complexes from being misdirected to other cells having an affinity for lipophilic groupings. Examples of such groupings include sugars such as lactose, maltose, galactose and polyethyleneglycol.

When determining the molar ratio of internalizing factor to bonding factor within the conjugates, care should be taken to ensure that complexing of the nucleic acid or acids takes place and that the complex formed is assured of being bound to the cell and conveyed into the cell. The conjugates may be defined by simple preliminary trials in which conjugates of varying composition are investigated for their efficiency.

The particular ratio selected will depend primarily on the size of the polycation molecule and the number and distribution of the positively charged groupings, criteria which are coordinated with the size, structure and any possible modifications of the nucleic acid or acids to be transported.

After the conjugates have been constructed and synthesized and the optimum ratio of conjugate to DNA for the efficiency of transferrinfection has been determined, it is possible to determine, by means of titrations, the quantity of conjugate fraction which can be replaced by free substance having an affinity for nucleic acid. If polycations are used both as the bonding factor and as the free substance having an affinity for nucleic acid the polycations may be identical or different.

The complexes according to the invention may be prepared by mixing the components nucleic acid, internalizing factor/bonding factor conjugate and free substance having an affinity for nucleic acid, all of which may be present in the form of dilute solutions. If polycations are used as the bonding factor and at the same time as the free substance having an affinity for nucleic acid, it is generally advisable first to prepare a mixture of conjugates with free polycations and then to combine this mixture with DNA. The optimum ratio of DNA to the particular conjugate/polycation mixture is determined by titration experiments, i.e. In a series of transfection experiments with a constant quantity of DNA and increasing amounts of conjugate/polycation mixture. The optimum ratio of conjugate to polycations in the mixture is obtained by application or by comparing the optima of the mixtures used in the titration experiments.

The DNA complexes may be prepared at physiological saline concentrations. However, it is also possible to use higher salt concentrations (possibly 2M NaCl) and subsequently adjust them to physiological conditions by slow dilution or dialysis.

The most suitable sequence, according to the particular embodiment of the invention, for mixing the components nucleic acid, conjugate and non-covalently bound free substance having an affinity for nucleic acid is determined in each individual case in preliminary trials. In some cases it may prove advisable first to complex the nucleic acid with the conjugate and only then to add the free substance having an affinity for nucleic acid, e.g. the polycation, e.g. in the case of transferrin-ethidium dimer conjugates and polylysine.

In one embodiment of the invention the internalizing factor is transferrin and the bonding factor is a polycation. The nucleic acid is taken up in the form of complexes in which transferrin/polycation conjugates are complexed with nucleic acid, the free substance having an affinity for nucleic acid being polycation which is contained in the complexes in a non-covalently bound form, the free polycation being either identical to or different from the polycation contained in the conjugate.

The word "transferrin" refers both to the natural transferring and also to those transferrin modifications which are bound by the receptor and transported into the cell.

When determining the molar ratio of transferrin:polycation within the conjugates care should be taken to ensure that complexing of the nucleic acid or acids takes place and it is ensured that the complex formed will be bound by the transferrin receptor and conveyed into the cell; this can easily be checked by simple experiments carried out from one case to the next.

The following compounds may be used as cationic substances within the conjugates:

a) Protamines: These may be of natural origin or produced by the recombinant method, while multiple copies may be produced or modifications may be made in the molecular size and amino acid sequence. Corresponding compounds may also be chemically synthesized. When synthesizing a synthetic protamine, for example, the procedure may involve replacing amino acid groups which in the natural protamine have functions which are undesirable for the transporting function (e.g. condensation of DNA to form larger aggregates), by other suitable amino acids and/or providing, at one end, an amino acid (e.g. cysteine) which permits the desired conjugation with transferrin.

b) Histones: Natural and synthetic histones or fragments thereof may be used, while with regard to the production and modifications thereof the remarks made above in relation to protamines apply here as well.

c) Synthetic polypeptides such as homologous polypeptides (polylysine, polyarginine) or heterologous polypeptides (consisting of two or more representatives of positively charged amino acids).

d) Non-peptide polycations such as polyethyleneimines.

The size of the polycations depends primarily on the nucleic acid which is to be transported.

The transferrin-polycation conjugates may be produced chemically or, if the polycation is a polypeptide, by the recombinant method.

Coupling by the chemical method can be carried out in a manner known per se for the coupling of peptides and if necessary the individual components may be provided with linker substances before the coupling reaction (this procedure is necessary when there is no functional group suitable for coupling available at the outset, such as a mercapto or alcohol group). The linker substances are bifunctional compounds which are first reacted with functional groups of the individual components, after which coupling of the modified individual components is carried out.

Depending on the desired properties of the conjugates, particularly the desired stability thereof, coupling may be carried out by means of a) Disulphide bridges, which can be cleaved again under reducing conditions (e.g. using succinimidylpyridyldithiopropionate (Jung et al., 1981)).

b) Using compounds which are largely stable under biological conditions (e.g. thioethers, by reacting maleimido linkers with sulfhydryl groups of the linker bound to the second component).

c) Using bridges which are unstable under biological conditions, e.g. ester bonds, or acetal or ketal bonds which are unstable under slightly acidic conditions.

The production of the conjugates by the recombinant method offers the advantage of producing precisely defined, uniform compounds, whereas chemical coupling produces conjugate mixtures which then have to be separated. For preparation by the recombinant method, protein and histone conjugates are particularly preferred.

The recombinant preparation of the conjugates can be carried out using methods known for the production of chimeric polypeptides. The polycationic peptides may vary in terms of their size and amino acid sequence. Production by genetic engineering also has the advantage of allowing the transferrin part of the conjugate to be modified, by increasing the ability to bind to the receptor, by suitable mutations, for example, or by shortening the transferrin fraction to the part of the molecule which is responsible for the binding to the receptor.

If the internalizing factor is a glycoprotein, e.g. transferrin, it may be bound to the bonding factor via one or more carbohydrate chains of the glycoprotein.

Conjugates of this kind have the advantage that they are free from modifications which originate from the linker substances used. In the case of glycoproteins which have only one or a few carbohydrate groups suitable for coupling, e.g. transferrin, these conjugates also have the advantage that they are accurately defined in terms of their binding site for glycoprotein/bonding factor.

A suitable method of preparing glycoprotein-polycation conjugates is disclosed in German Patent Application P 41 15 038.4; it was described by Wagner et al., 1991.

The present invention has the advantage, inter alia, of increasing the efficiency of transferrin-protamine conjugates, which are, admittedly, in themselves less effective than polylysine conjugates but are relatively easy to produce by the recombinant method, to obtain conjugates of a defined composition. With regard to the transferrin-polycation conjugates which may be used, or the complexes with DNA and the preparation thereof, specific reference is made to the disclosure of EP-A 1 0388 758.

The information given above shows possible embodiments of the invention, using transferrin complexes, but is not specifically restricted to transferrin complexes.

In order to determine suitable conditions for transfection the following procedure may be used, which is illustrated by way of example using transferrin-polycation conjugates: starting from a nucleic acid which is to be transported into the cell and which is defined by the application (transfer of genes or gene sections, inhibition of cell functions by means of antisense-oligonucleotides, etc.), transferrin-polycation conjugates are synthesized which can be complexed with the nucleic acid and taken up into the cell via the transferrin receptor. In the particular cell system in which transfection is to take place, first of all the suitable conditions for transfection are selected, particularly with regard to the cells to be transfected or the state of these cells, e.g. conditions which bring about an increase in the number of transferrin receptors and/or inhibit the breakdown of nucleic acid in cell organelles, particularly lysosomes.

It is not critical whether the increase in the uptake of transferrin-polycation/nucleic acid complexes can be attributed solely to the increase in the number of transferrin receptors by means of direct or indirect action on the receptor (increasing the receptor synthesis, e.g. by increasing the rate of transcription, inhibiting the breakdown of mRNA or an increased translation rate of mRNA, reduction in the breakdown of the receptor or combinations of such mechanisms). Other mechanisms may also be involved in this effect, e.g. an increase in the affinity of transferrin for its receptor and/or an increase in the recycling rate of t he transferrin receptor and/or the inhibition of competition from native transferrin with the transferrin-polycation/nucleic acid complexes for binding to the transferrin receptor. What matters is that the conditions to which the cells are exposed result in an increase in the uptake of the transferrin-polycation-nucleic acid complexes. The definition "conditions which bring about an increase in the number of transferrin receptors" thus also covers those conditions which bring about an increase in the efficiency of transferrinfection by means of the mechanisms mentioned above.

Suitable conditions to which the cells are exposed in order to increase the number of transferrin receptors may, for example, consist in bringing the cells into contact with substances capable of lowering the hemoconcentration within the cell.

These are preferably substances which bring about a reduction in the hemoconcentration in the cell by;

a) inhibiting the protoporphyrin IX biosynthesis;

b) preventing hemoformation c) promoting hemo-decomposition.

The substances of group a) include succinylacetone, while the increase in the number of transferrin receptors can probably be attributed to the inhibition of protoporphyrin IX biosynthesis. The substances of group b) include those which induce an iron deficiency in the cell, e.g. the iron chelate forming agent desferrioxamine, which presumably causes an increase in the number of transferrin receptors because the conversion of protoporphyrin IX into heme is prevented. Fundamentally, all the substances, particularly iron chelating agents, which can be absorbed into the cell and which have the effect of desferrioxamine on the quantity of iron available for heme formation, are suitable for increasing the number of transferrin receptors.

The group of substances mentioned are important, for the use of transferrin complexes within the scope of the present invention, in as much as they are obviously suitable for eliminating the competition between native transferrin and the transferrin-polycation/nucleic acid complexes for binding to the receptor. By pretreating cells—in vivo or in vitro—with such substances the iron which is not bound to the transferrin can be removed, so that there is no more iron available for the transferrin excluded from the cell and this transferrin therefore does not compete, as an apotransferrin, with the transferrin-polycation/nucleic acid complexes for binding to the transferrin receptor. On the other hand, the removal of free iron can prevent a reduction in the number of transferrin receptors caused by the presence of free iron.

Group c) includes substances which induce or stimulate heme degradation, and consequently the cell, by increasing the concentration of transferrin receptors or the affinity of transferrin for its receptor or the receptor recycling rate. (It has been found that, by means of these substances, it is possible to improve the uptake of DNA into the cells, while combinations of substances of groups a) to c) had an additive effect, determined by means of the activity of the reporter gene expressed.)

Within the scope of the present invention it may also be useful to create conditions under which the degradation of the nucleic acid in the cells is inhibited. Such conditions may be provided by the addition of so-called lysosomatropic substances. These substances are known to inhibit the activity of proteases and nucleases in lysosomes and are thus able to prevent the degradation of nucleic acids, while the definition of the properties of lysosomatropic substances also includes their potential ability to enable or facilitate the release of nucleic acid from cell organelle membranes within the cell.

These substances include chloroquin, monensin, nigericin, ammonium chloride and methylamine.

The necessity of using a substance selected from the group of lysosomatropic substances will depend in particular on the type of cell to be treated. The suitability of a substance from this group for the purposes of the present invention and the concentration thereof or the time it is allowed to act on the cells will depend, on the one hand, on their toxicity for the cells and, on the other hand, on whether these substances affect the cycling of the transferrin receptor, e.g. by blocking the vesicle fusion and thereby preventing the decoding of the receptor. With regard to the use of substances which inhibit the breakdown of nucleic acid, it was found that it is not essential for all cell types in order to achieve efficient transferrinfection.

When using lysosomatropic substances it is therefore necessary to test the amount required or their suitability for enhancing transferrinfection in preliminary trials. If necessary, these substances may be used in short bursts, for a short period of action, in order to rule out or minimize any effect which may damage the cell.

In another embodiment of the present invention the internalizing factor is a protein capable of binding to CD4 ("CD4 binding protein", "CD4BP"). Within the scope of the unpublished Austrian Patent Application A1110/90 it had been found that the receptor used by the HIV virus during infection, namely CD4, can be used for transporting nucleic acids into the cell, by complexing the nucleic acid which is to be introduced into the cell with a protein-polycation-conjugate the protein content of which is a CD4 binding protein. The CD4BP used may be any of the monoclonal antibodies against CD4 or fragments thereof which bind to CD4, e.g. Fab' fragments (Pelchen-Matthews et al., 1989).

These include monoclonal anti-CD4 antibodies which have a gp120 epitope which competes with the virus for binding to this epitope.

Instead of conventional monoclonal antibodies or fragments thereof, it is possible to use CD4-antigen binding antibody fragments consisting of a combination of segments of the heavy and light chain or possibly the heavy chain on its own. As CD4BPs it is also possible to use HIV-1-gp120 or homologous proteins of related retroviruses or fragments thereof. Suitable gp120 fragments are those which are capable of binding to CD4 (Lasky et al., 1987), e.g. the 95-kDa and 25-kDa fragments, which have been shown to bind to CD4 (Nygren et al., 1988). Such fragments may be obtained, for example, either by producing the entire gp120 protein by the recombinant method and subsequently cleaving it proteolytically or, alternatively, by recombinant preparation of the fragments themselves.

With regard to the polycation portion of the conjugates or the non-covalently bound free substances having an affinity for nucleic acid, the remarks made above for the transferrin-polycation conjugates apply in principle.

Regarding the molar ratio of CD4BP to polycation within the conjugates and regarding the requirements of complexing of the nucleic acid or acids, binding by CD4 and conveying into the cells, basically the remarks made above for the use of transferrin-polycation conjugates apply. Using CD4-expressing cell lines which are brought into contact with the conjugates and are then investigated for the presence of nucleic acid in the cell, e.g. by Southern blot analysis, hybridizing with radioactively labelled complementary nucleic acid molecules, by amplifying using PCR or by detecting the gene product of a reporter gene it is possible to examine the performance of the complexes. After determining the optimum ratio of CD4BP to polycation for efficient transferrinfection, it is possible to determine, using an analogous procedure to that used in transferrin-conjugates, by means of titrations, the quantity of conjugate component which can be replaced by free substance having an affinity for nucleic acid, while in this embodiment of the invention too, the free substance having an affinity for nucleic acid may possibly be different from the polycation component of the conjugate.

Even if CD4BP-bonding factor conjugates are used it may be advisable to improve the efficiency of the system by using substances which inhibit the degradation of nucleic acid in the cells, while with regard to the suitability and necessity of such measures the same considerations apply as in the use of transferrin-polycation conjugates.

In the tests which were carried out within the scope of the present invention, plasmid-DNA containing the *Photinus pyralis* luciferase gene was used as an example of nucleic acid to be transported into the cell. This DNA is, in practice, particularly useful for preliminary trial s which serve to determine the particular conditions required in individual cases, e.g. for a certain cell type.

In therapeutic use, the nucleic acid is defined above all by the biological effect which is to be achieved in the cell, while in applications in the scope of gene therapy it is defined by the gene or gene section which is to be expressed, e.g. in order to substitute a defective gene, or by the target sequence of a gene which is to be inhibited. The nucleic acids to be transported into the cells may be DNAs or RNAs; there are no restrictions on the nucleotide sequence. As therapeutically effective inhibiting nucleic acids, gene constructs in particular are transported into the cell for the purpose of inhibiting specific gene sequences. They include gene constructs by which antisense RNA or ribozymes are transcribed.

Examples of genes which may be used in gene therapy and which can be locked into the cell by means of the present invention as a component of gene constructs include facto IX (used in hemophilia; Kurachi and Davie, 1982), adenosine deaminase (SCID; Valerio et al., 1984), α-1 antitrypsin (lung emphysema; Ciliberto et al., 1985) or the "cystic fibrosis transmembrane conductance regulator gene" (Riordan et al., 1989). These examples do not constitute a restriction of any kind.

With regard to the size of the nucleic acids, a wide range may be used; according to the present invention nucleic acid molecules of the order of about 0.3 kb to about 50 kb or more can be conveyed into the cells.

According to another aspect the invention relates to pharmaceutical compositions containing a complex with a nucleic acid specifically inhibiting a gene as the active component. Complexes according to the invention containing an inhibiting nucleic acid of this kind, e.g. in the form of antisense oligonucleotides, antisense oligonucleotide analogues or ribozymes or the DNAs coding for them, optionally together with a carrier nucleic acid such as tRNA, e.g. in the form of lyophilizates, may be used in order to inhibit pathogenic viruses in humans or animals, such as HIV or related retroviruses, oncogenes or other key genes which control the growth and/or differentiation of cells, e.g. the c-fos gene or the c-myc gene.

Another field of application of the pharmaceutical preparations according to the invention consists in fighting diseases by inhibiting the production of undesirable gene products, e.g. the major plaque protein which occurs in Alzheimer's disease, or proteins which cause autoimmune diseases.

The dosage of the internalizing factor-bonding factor/nucleic acid complexes which contain free substance having an affinity for nucleic acid according to the invention will depend particularly on the concentration of cells to be treated and on the particular nucleic acid which is to be inhibited. The quantity of complexes used also depends, for example, on whether the nucleic acid as such is the active component or whether, e.g. in the case of ribozymes, it is imported into the cell as a gene and amplified in the cell.

The optimum dosage used for a specific indication in each type of cell is determined in preliminary trials for each individual case.

For therapy the substances may be administered in vivo or ex vivo. In vivo application for the treatment of tumors may, for example, consist in injecting into the tumor tissue a solution of a suitable complex containing, for example, as the nucleic acid a ribozyme directed against an activated oncogene.

Ex vivo treatment may be considered, for example, for treating leukemic cells. The procedure used may for example consist in taking bone marrow or peripheral blood from the patient. The leukemic cells are then selectively treated, under optimum conditions for transferrinfection (e.g. after pretreatment with desferrioxamine), with transferrin-polycation/nucleic acid complexes which contain as nucleic acid component an antisense oligonucleotide or ribozyme which neutralizes the oncogene activity. Finally, the bone marrow or blood is reimplanted into the body.

With the aid of the present invention it is possible to achieve an improved activity with the therapeutic use of pharmaceutical compositions containing internalizing factor/bonding factor-nucleic acid complexes, by improving the introduction of the effective nucleic acid into the cells or intensifying the expression thereof.

EXAMPLE 1

Figure 1A:
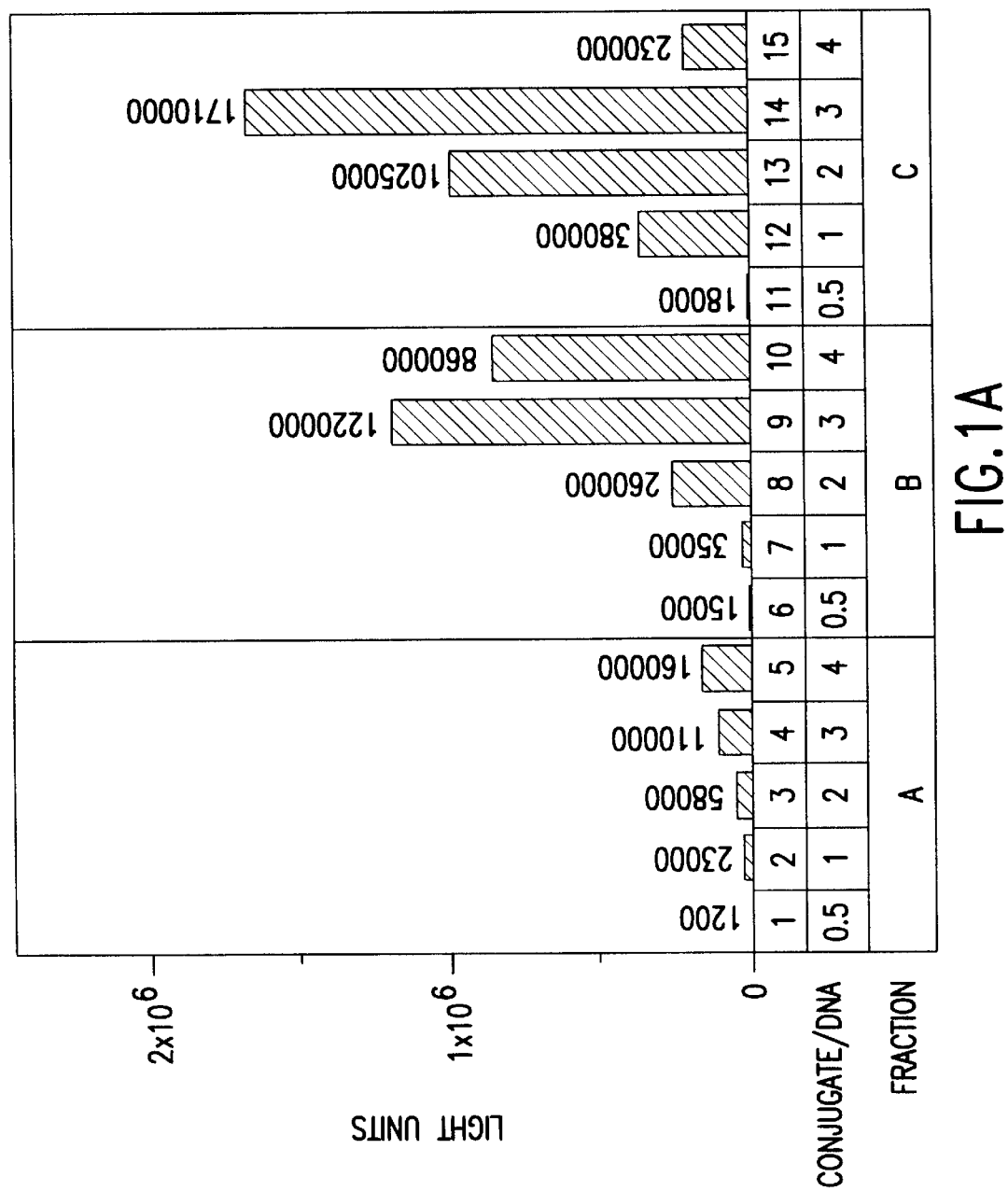
FIG. 1A: Determining the optimum ratio of transferrin-polylysine-conjugates/DNA (transferrin-polylysine 200)

Preparation of transferrin-polylysine 200 and transferrin-polylysine 450 conjugates (TfpL200 and TfpL450)

Coupling was carried out using methods known from the literature (Jung et al., 1981) by introducing disulphide bridges after modification with succinimidylpyridyl-dithiopropionate. The procedure used was that described in EP-A 1 0388 758, with only a slight modification to the method of isolation, as a result of which a higher yield of conjugate was obtained.

a) 3-(2-Pyridyldithio)propionate-modified transferrin 6 ml of a solution of 120 mg (1.5 µMol) of transferrin gel-filtered over Sephadex G-25 (human transferrin, Sigma, free from iron) in 3 ml of 0.1M sodium phosphate buffer (pH 7.8) were mixed, with vigorous shaking, with 200 µl of a 15 mM ethanolic solution of succinimidyl 3-(2-pyridyldithio) propionate (3 µM, SPDP, Pharmacia) and left to react for 1 hour at ambient temperature with occasional shaking. Lower molecular reaction products and residues of reagent were removed through a gel column (Sephadex G-25, 14×180 mm, 0.1M sodium phosphate buffer pH 7.8) and 7 ml of the product fraction were obtained; the content of pyridyldithio-propionate residues bound to transferrin was determined by means of an aliquot after reduction with dithiothreitol by photometric measurement of the quantity of pyridin-2-thione released and amounted to about 2.6 µMol.

b) Preparation of modified polylysine 200 (pL200) and polylysine 450 (pL450)

A gel-filtered solution of 0.57 µMol pL200 (with an average polymerization level of 200 lysine groups, with fluorescent labelling) in 3 ml of 20 mM sodium acetate buffer was adjusted to pH 7.9 by the addition of 300 µl of 1M HEPES buffer. With vigorous stirring, 204 µl of a 10 mM ethanolic solution of SPDP (2.04 µMol) were added. One hour later, 500 µl of 1M sodium acetate, pH 5, were added. In order to separate off low molecular substances, the mixture was filtered over Sephadex G-25 (eluant: 20 mM sodium acetate buffer pH 5.0). A solution was obtained which contained 0.54 µMol of pL200 with 1.86 µMol of dithiopyridine groups (3.5 linkers per polylysine chain), the solution was adjusted to pH 7 approximately with buffers, 36 mg of dithiothreitol were added and the mixture was left to stand for 1 hour at ambient temperature under argon in the dark. 400 µl of 3M sodium acetate buffer, pH 5.0, were added and separated off from the excess reducing agent by further gel filtration (Sephadex G-25, 14×180 mm column, 15 mM sodium acetate buffer pH 5.0). 4 ml of product solution were obtained, containing 0.50 µmol of fluorescent-labelled polylysine containing 1.84 µMol of mercapto groups (photometric measurement using Ellman's reagent, 5.5'-dithiobis(2-nitrobenzoic acid).

Analogously, 0.20 µMol of pL450 (with an average polymerization level of 450 lysine groups) were modified with 0.70 µMol SPDP, to obtain a product of 0.18 µMol of pL450 with 0.57 µMol of dithiopyridine groups (3.2 linkers per polylysine chain). The dithiopyridine groups were reduced with dithiothreitol as stated above for polylysine 200. 0.175 µmol of polylysine were obtained, modified with 0.57 µmol of mercapto groups.

c) Preparation of transferrin-polylysine-conjugates

Transferrin-pL200 conjugates were prepared by mixing 1.06 µMol of the modified transferrin obtained in a) (in 100 mM HEPES buffer pH 7.9) with 0.20 µMol of the modified pL200 obtained in b) (in 30 mM sodium acetate buffer) with the exclusion of oxygen in an argon atmosphere. Similarly, transferrin-polylysine 450 conjugates were prepared, starting with 0.61 µMol of modified transferrin according to Example 1a) (in 100 mM HEPES pH 7.9) and 0.12 µMol pL450 (in 30 mM sodium acetate buffer).

After 18 hours at ambient temperature the conjugates were isolated from the reaction mixture by cation exchange chromatography (Pharmacia Mono S column HR 10/10; gradient elution, buffer A: 50 mM HEPES pH 7.9, buffer B: buffer A plus 3M sodium chloride). It was found that in order to obtain polycation conjugates it was essential to add sodium chloride to the reaction mixture (final concentration 0.6M in the case of TfpL200 or 1M in the case of TfpL), before the column was charged, and to begin the gradient at this salt concentration. The product fractions were eluted at salt concentrations of about 1.4M in the case of TfpL200 and about 2M in the case of TfpL450. After dialysis against HBS (HEPES buffered saline solution: 20 mM HEPES, 150 mM NaCl, pH 7.4) the conjugate fractions were obtained in a total yield of 80% (TfpL200) and 64% (TfpL450) respectively. The conjugate fractions are characterized in more detail in terms of the ratio of transferrin to polylysine in FIGS. 2A and 2B.

Iron was incorporated into the conjugates by adding 3 to 10 μl of 10 mM iron citrate[III], 200 mM citrate, adjusted to pH 7.8 using sodium bicarbonate) to the samples, per mg of transferrin component.

EXAMPLE 2 a) Determining the optimum ratio of transferrin-polylysine conjugate to DNA

Each of the conjugates obtained in Example 1 was tested by titration for its optimum ratio of conjugate to DNA for the purpose of DNA introduction and expression. The DNA used was pRSVL plasmid DNA (De Wet et al., 1987), prepared by Triton-X lysis standard method (Maniatis), followed by CsCl/EtBr equilibrium density gradient centrifugation, destaining with butanol-1 and dialysis against 10 mM tris/HCl, pH 7.5, 1 mM EDTA (cf. EP-A 1 0388 758).

Figure 1B:
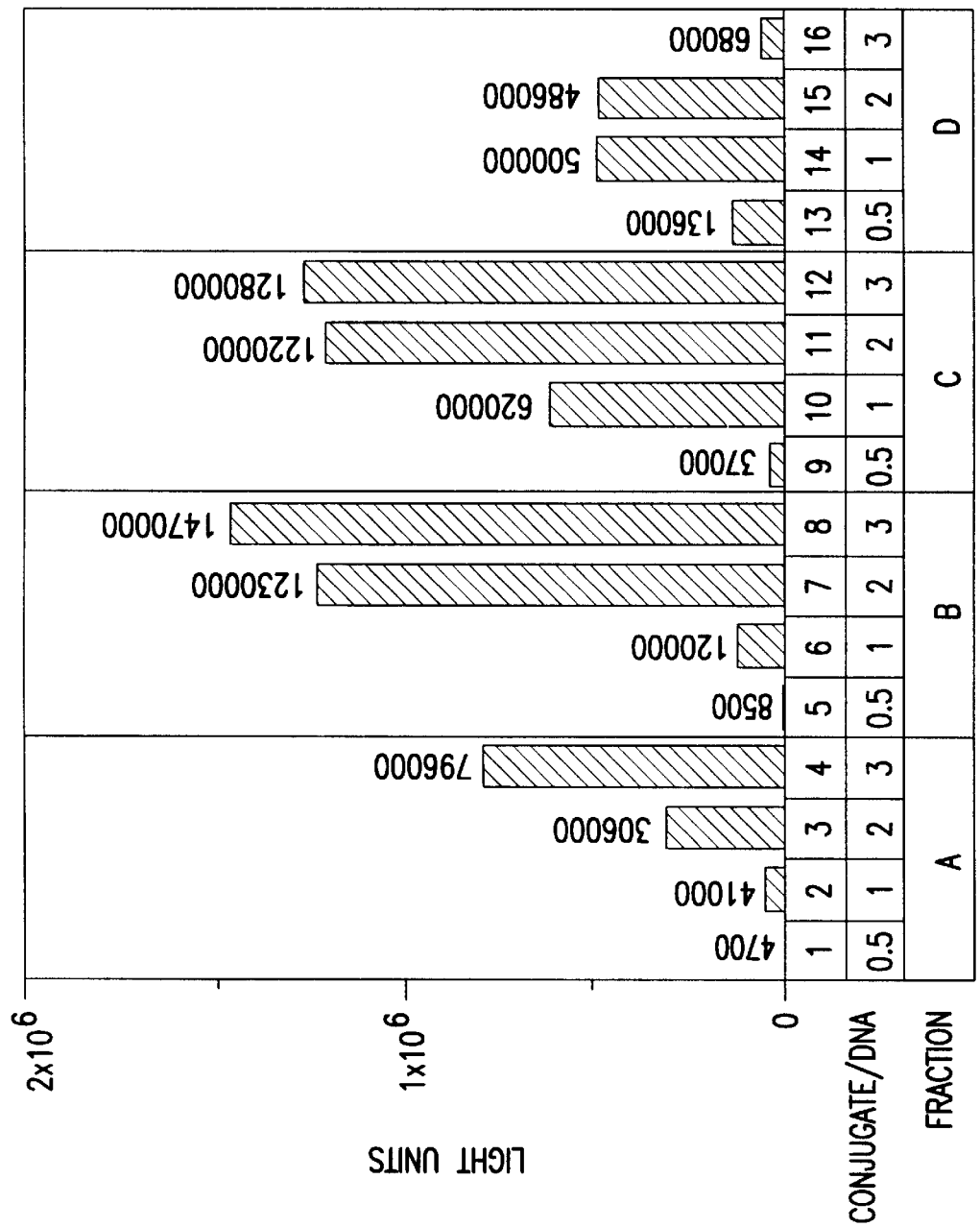
FIG. 1B: Determining the optimum ratio of transferrin-polylysine-conjugates/DNA (transferrin-polylysine 450)

The transferrin-polycation/DNA complexes used in the titrations were prepared by mixing a constant quantity of pRSVL-plasmid DNA, specifically 10 μg in the case of the TfpL200 fractions and 6 μg in the case of the TfpL450 fractions, with increasing amounts of the particular conjugate fractions. FIG. 1A (TfpL200) and FIG. 1B (TfpL450) show the ratios of amounts selected for carrying out the titrations, the amounts being designated as the mass ratio of DNA to the transferrin contained in the conjugate and the conjugate fractions with A–C and A–D respectively (cf. FIG. 2). The complexes were prepared in 500 μl reaction volume of HBS (150 mM NaCl, 20 mM HEPES pH 7.4), incubated for 30 minutes at ambient temperature and added to 2 ml of cell culture. For the transfections, cells of the erythroleukemia cell line K562 were cultivated in RPMI 1640 medium supplemented with 10% fetal calves' serum, 100 IU/ml penicillin, 100 μg/ml streptomycin and 2 nM glutamine, at a density of $2-5 \times 10^5$ cells per ml. The cells were pretreated 18–24 hours before the transfection with 50 μM desferrioxamine in order to increase the number of transferrin receptors on the cell. Transfections were carried out with $5 \times 10^5$ cells in 2 ml of medium in the presence of 100 μM chloroquin. After 4 hours incubation at 37° C. the cells were taken up in fresh medium, incubated at 37° C. and harvested 18 hours later for the measurement of luciferase. FIG. 1 gives the luciferase activity of cell extract aliquots (about 15–20% of the total extract) standardized to protein content.

b) Influence of the transferrin-polylysine ratio in the conjugates on the efficiency of transferrinfection Three TfpL200 conjugate fractions A–C with a different average number of transferrin molecules per polylysine chain were used in the optimum quantity determined in a) (40 μg for fraction A, 30 μg for fractions B and C) for complex forming with 10 μg of pRSVL DNA. $10^5$ cells were transfected with the resulting complexes under standard conditions as stated above and the gene expression was determined by measuring the luciferase activity of cell extract aliquots, standardized for protein content.

Transferrinfection experiments with the four TfpL450 fractions A–D were methodically carried out in exactly the same way, except that only 6 μg of DNA were used and were mixed with the quantities of conjugate found to be optimum, namely 18 μg (fractions A–C) and 12 μg (fraction D).

Figure 2A:
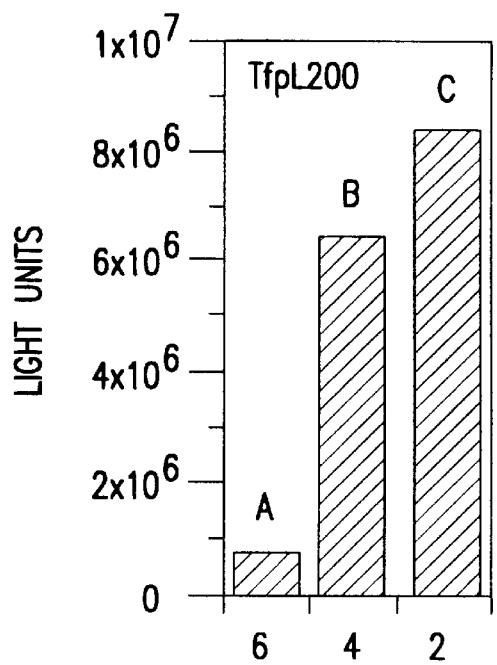
FIG. 2: (panels A and B) Effect of the ratio of transferrin to polylysine on the efficiency of gene transfer (A: transferrin-polylysine 200; B: transferrin-polylysine 450)
Figure 2B:
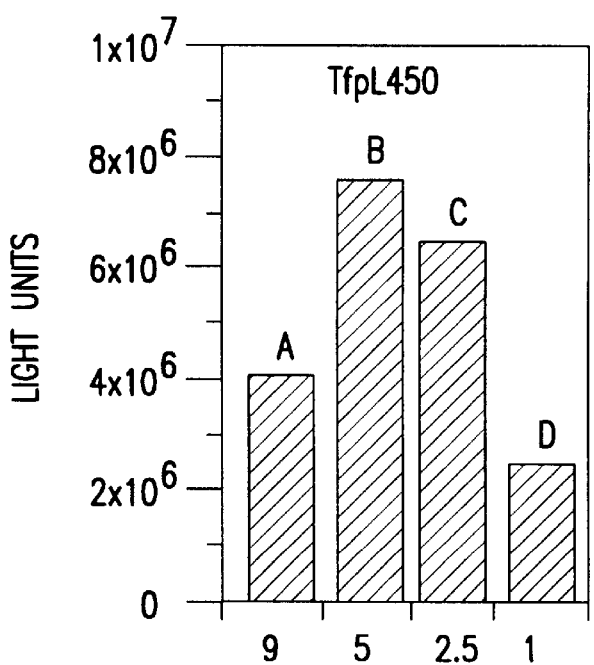

The results of these experiments are shown in FIG. 2 (the values for the luciferase activity refer to the total extract). This clearly shows that fractions with a low number of transferrin molecules per polylysine molecule are more efficient. FIG. 2A: conjugates C with a molar ratio of transferrin to polylysine of 2:1 are 10 times more effective than conjugates A with a ratio of 6:1. FIG. 2B: the experiments show that when the long transferrin-pL450 conjugate is used conjugates with a ratio of 9:1 are less active than those with a ratio of 5:1, while these are in turn comparable in their activity with conjugates having a ratio of Tf:pL of 2.5:1. When the polylysine content is even higher (ratio 1:1), however, the activity falls off again.

EXAMPLE 3

Determining the minimum number of transferrin molecules needed per DNA molecule

Figure 3:
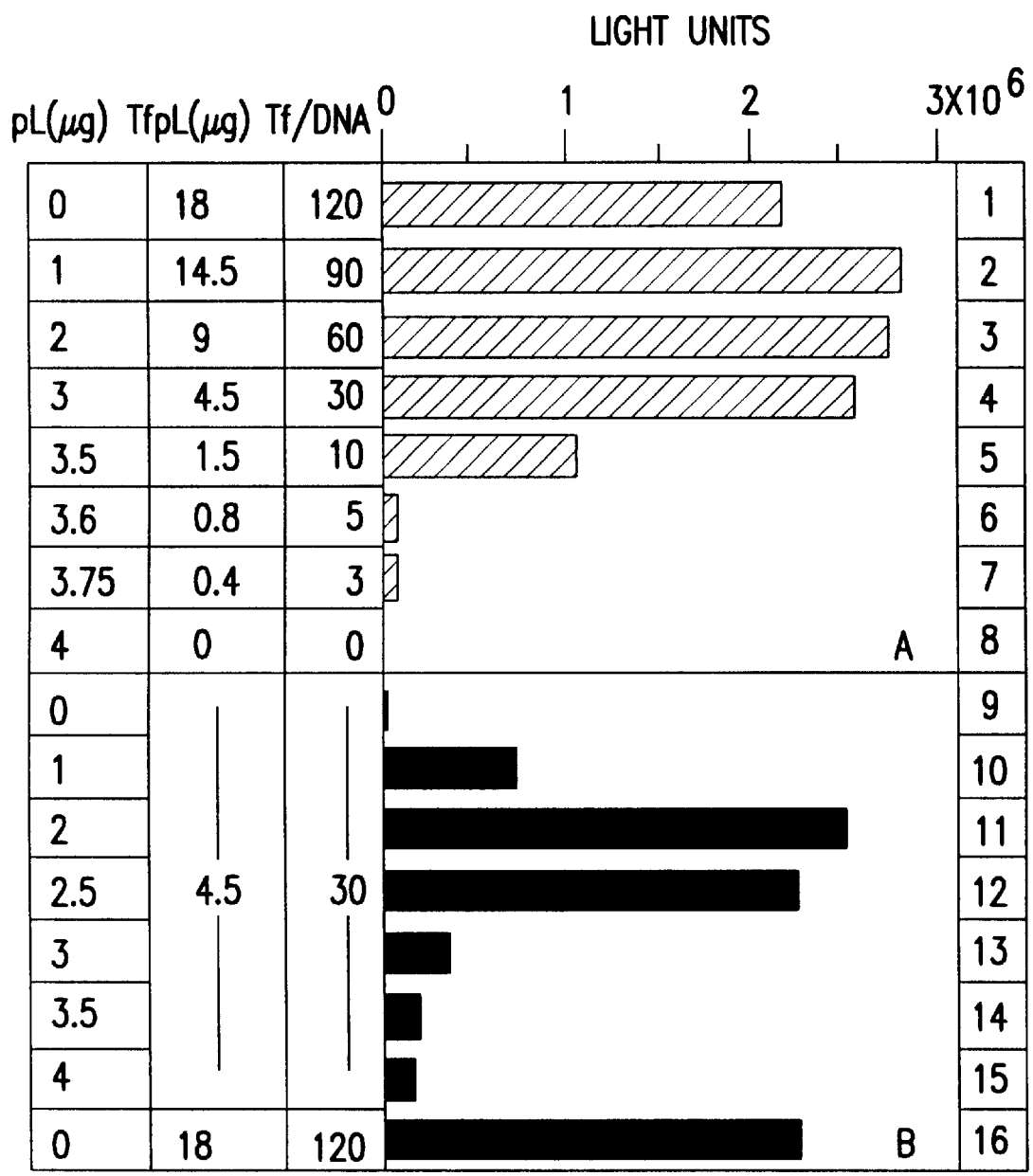
FIG. 3: (panels A and B) Determining the minimum number of transferrin molecules required per DNA molecule. A: replacement of increasing amounts of conjugate by non-conjugated polylysine. B: addition of non-conjugated polylysine to a constant optimum quantity of conjugate

When carrying out the experiments within the course of this Example the starting premise was that the high number of about 120 transferrin molecules per "doughnut" (this number being a statistical value calculated from the mass ratio of conjugate to DNA) ought not to be necessary for the functioning of receptor-mediated endocytosis. To test the accuracy of this premise, tests were carried out in which an increasing amount of the transferrin conjugate was replaced by non-modified polycation, while the total polylysine quantity was maintained at the predetermined optimum (about 4 μg of polylysine per 6 μg of DNA). The efficiency of the transferrinfection (transfections and luciferase activity measurements were carried out analogously to Example 2) remain the same or increased slightly when the conjugate content of the sample was reduced and replaced by polylysine (the results obtained for poly(D)lysine and poly(L) lysine agreed). If, however, the transferrin content fell below 10–15 molecules per molecule of DNA, the efficiency of transferrinfection was also sharply reduced (FIG. 3A samples 5 to 8). A minimum of 10 to 15 transferrin molecules per molecule of DNA was found to be necessary for efficient gene transfer. If no conjugate is added to the sample, the gene transfer falls virtually to zero. The results of the experiments are shown in FIG. 3A: columns 1 to 8 show the expression of the luciferase gene after transferrinfection, while during the complex formation with 6 μg of DNA the optimum quantity of TfpL200 of 18 μg was gradually replaced by increasing quantities of p(D)L240. (The levels given in FIG. 3 for the luciferase activity relate to the total extract.)

EXAMPLE 4

In a further series of experiments, a constant amount (4.5 μg) of transferrin-polycation conjugate was used as starting material, corresponding to about ¼ of the amount found to be optimum in Example 2a). The conjugate was mixed with increasing amounts of polylysine 90 (pL90) and added to a constant quantity of DNA (6 μg). Transfections and luciferase measurement were carried out as in the preceding Examples; the results of the tests are shown in FIG. 3B. In the experiments according to columns 9 to 15, complexes of 6 μg pRSVL were prepared with 4.5 μg of TfpL200C, to which were added increasing amounts of pL90. (Column 16 shows the results of the control experiment with 6 μg of pRSVL and the optimum quantity (18 μg) of TfpL200C.) As can be seen from FIG. 3B, the effectiveness of transfection, which had fallen to about 1/100 of the optimum result when using the suboptimum starting quantity of TfpL, could be reestablished by adding free pL90.

EXAMPLE 5

As in Example 4 a series of tests were carried out starting from a suboptimum quantity of 6 μg of DNA complexed with a quantity of 9 μg of TfpL200, to investigate how different amounts of various polycations affected the uptake of DNA. Transfections and the measurement of the efficiency of DNA import were carried out under standard conditions as given above. The free polycations used were various poly(L)lysines with an average chain length of 55, 90, 200 or 450 lysine monomers, poly(D)lysine with an average chain length of 240 lysines (all the polylysines were obtained in the form of hydrobromide salts from Sigma), protamine (salmon protamine sulphate, free from histones, Sigma), the histones H1, H3 and H4 (obtained from calves' thymus, Boehringer Mannheim). Table 1 shows the quantities of free cations used and the relative efficiency of transferrinfection of 6 μg of DNA complexed with a mixture of 9 μg of TfpL200 plus the quantities of polycations specified. The numbers in the Table indicate %, based on the efficiency of complexes prepared using the optimum amount (18 μg) of TfpL200.

This series of experiments showed that the addition of polylysines and natural protamine and the histones investigated achieved a DNA import efficiency at least equivalent to that obtained when using the conjugates which had been found to be optimum. The exceptions were spermine and spermidine, which were incapable of re-establishing the degree of DNA uptake at the physiological salt concentration of the tissue culture system.

EXAMPLE 6

Preparation of transferrin conjugates with a synthetic protamine analogue

Conjugates between transferrin and a synthetic protamine of the sequence

Lys-Pro-Arg-Ala-Arg-Arg-Ser-Ser-Ser-Arg-Pro-Val-Arg-Arg-Ser-Ser-Arg-Pro-Ala-Val-Ser-Ala-Arg-Arg-Arg-Ser-Arg-Gly-Gly-Ser-Arg-Arg-Gly-Gly-Gly-Cys were synthesized by coupling through disulphide bridge formation between the C-terminal cysteine of the peptide and 3-(2-pyridyldithio)propionate-modified transferrin.

a) Preparation of synthetic protamine

The polypeptide was synthesized by solid phase synthesis using an automatic peptide synthesizer (Applied Biosystems 431A) under the conditions recommended by the manufacturer (fluorine methoxycarbonyl technique (Fmoc); the side chains used were t-butyl for serine and cysteine, t-butoxycarbonyl for lysine and pentamethyl-chromansulphonyl for arginine). The crude peptide obtained was subjected to gel filtration (Sephadex G-25 PD 10 column, eluant: 10% acetic acid), the solution obtained was further fractionated by reverse phase HPLC (Merck-Hitachi, Nucleosil 100-5C18, 8×250 mm, solvent A: 0.1% trifluoroacetic acid in water, solvent B: 0.1% trifluoroacetic acid in 60% acetonitrile; gradient elution with 0 to 100% B in 45 minutes; flow rate 2 ml/min). The product eluted at a concentration of 43% solvent B and was further purified by cation exchange chromatography (Pharmacia MonoS HR 10—10 column. Buffer A: 33 mM HEPES pH 7, buffer B: buffer A plus 1M NaCl; gradient elution, flow rate 0.5 ml/min.). The main peak, which eluted at a salt concentration of 0.81M, was desalinated and lyophilized by a further HPLC run (same conditions as before); the yield was 39.6 mg of pure peptide in the form of the trifluoroacetate salt. As the time of flight mass spectrum (plasma desorption mass spectrometry, PD-MS Instruments, Uppsala, Sweden) a value of 4018.4 (MH$^+$, molecule with a t-butyl-protected cysteine) was determined.

b) DNA binding test

It was confirmed by Gel Mobility Shift Assay that the synthetic protamine prepared in a) binds to DNA. For this purpose, HindIII cut λ-DNA fragments were used (fragment sizes between 23120 bp and 564 bp, $^{32}$P labelled at the 3'-end by filling the overhanging ends with α$^{32}$P dATP by Klenow polymerase for 45 minutes at 37° C., isolation by ethanol precipitation after the addition of glycogen and sodium acetate). To each sample containing 2 μl (10 ng) of DNA were added 2.55 μl of a 100 mM HEPES buffer pH 7.3, containing 1M NaCl, and the samples were mixed with increasing amounts (3, 10, 30, 100, 300 and 1000 ng) of the synthetic peptide (as trifluoroacetate) or with 10, 30 or 100 ng of natural protamine in 10.5 μl of aqueous solution. After the addition of 2 μl of application buffer (0.25% bromophenol blue, 0.25% xylenecyanol and 30% glycerol in water) to each sample, the samples were subjected to electrophoresis on a 1% agarose gel with 1×TAE (40 mM trisacetate/1 mM EDTA, pH 8) eluant buffer at 50 V (42 mA). The gel was dried, then autoradiography was carried out for 2 hours at −80° C. using an XAR film (Kodak). A significant band shift was recorded even with 3 ng of the synthetic peptide, while with 10 ng a substantial band shift was recorded (the majority of the DNA was held back at the starting slot).

c) Preparation of conjugates between transferrin and synthetic protamine

Figure 4:
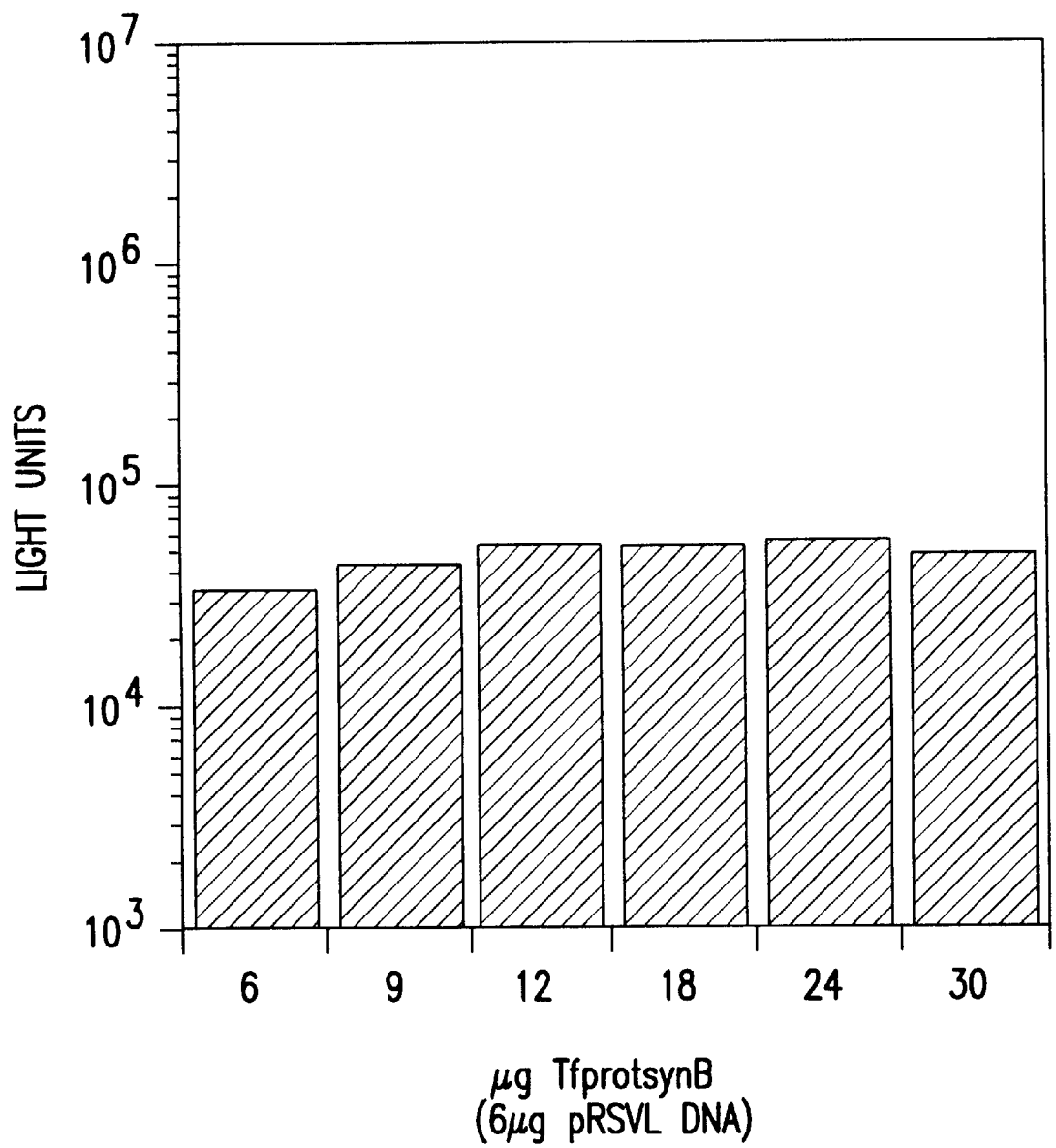
FIG. 4: Gene transfer by means of conjugates of transferrin and synthetic protamine

To 3 ml of a solution obtained after gel filtration of 100 mg (1.25 μmol) of human transferrin on a Sephadex G-25 column in 100 mM HEPES pH 7.3 were added 167 μl of a 15 mM ethanolic solution of succinimidyl 3-(2-pyridyldithio)propionate (SPDP; Pharmacia) and the solution was mixed thoroughly. After 1 hour at ambient temperature further gel filtration was carried out (Sephadex G-25 column) using 20 mM HEPES pH 7.3 which yielded 4.6 ml of a solution of 1.14 μmol of transferrin, modified with 2.24 μmol of dithiopyridine linker. After the exclusion of oxygen this solution was mixed with 1.5 ml of a solution of 0.9 μmol of synthetic protamine in free mercapto form in 0.5% acetic acid. The reaction mixture was fractionated by cation exchange chromatography (Pharmacia Mono S-column HR10/10; gradient elution 0.5 ml/min, buffer A: 50 mM HEPES pH 7.3 buffer B: buffer A plus 3M NaCl, measured by determining the UV absorption at 280 nm). The excess of uncoupled transferrin was eluted first; the product fractions eluted during the gradient and were pooled into two conjugate fractions: Tf-protsyn A (eluted between 17% and 24% of buffer B) and Tf-protsyn B (eluted between 24% and 30% of buffer B). After dialysis against 25 mM HEPES pH 7.3 these yielded Tf-protsyn A with a content of 9 mg of modified transferrin (molar ratio of transferrin to protamine about 1:1.3, on the basis of amino acid analysis after protein hydrolysis) and Tf-protsyn B containing 13.5 mg of modified transferrin (molar ratio of transferrin to protamine about 1:1.8). The conjugates were obtained in a total yield of 0.28 μmol of transferrin. The conjugates obtained were complexed with pRSVL DNA, as described in Example 2; the ratios of DNA to conjugate are shown in FIG. 4. With the complexes obtained, transfections were carried out and described the preceding Examples. As shown in FIG. 4, the protamine conjugates have a significant although relatively minor capacity, compared with the transferrin-polylysine conjugates, to transport DNA into the cells. FIG. 4 shows the luciferase activity of cell extract aliquots (about 15 to 20% of the total extract), standardized for protein content.

EXAMPLE 7

Figure 5:
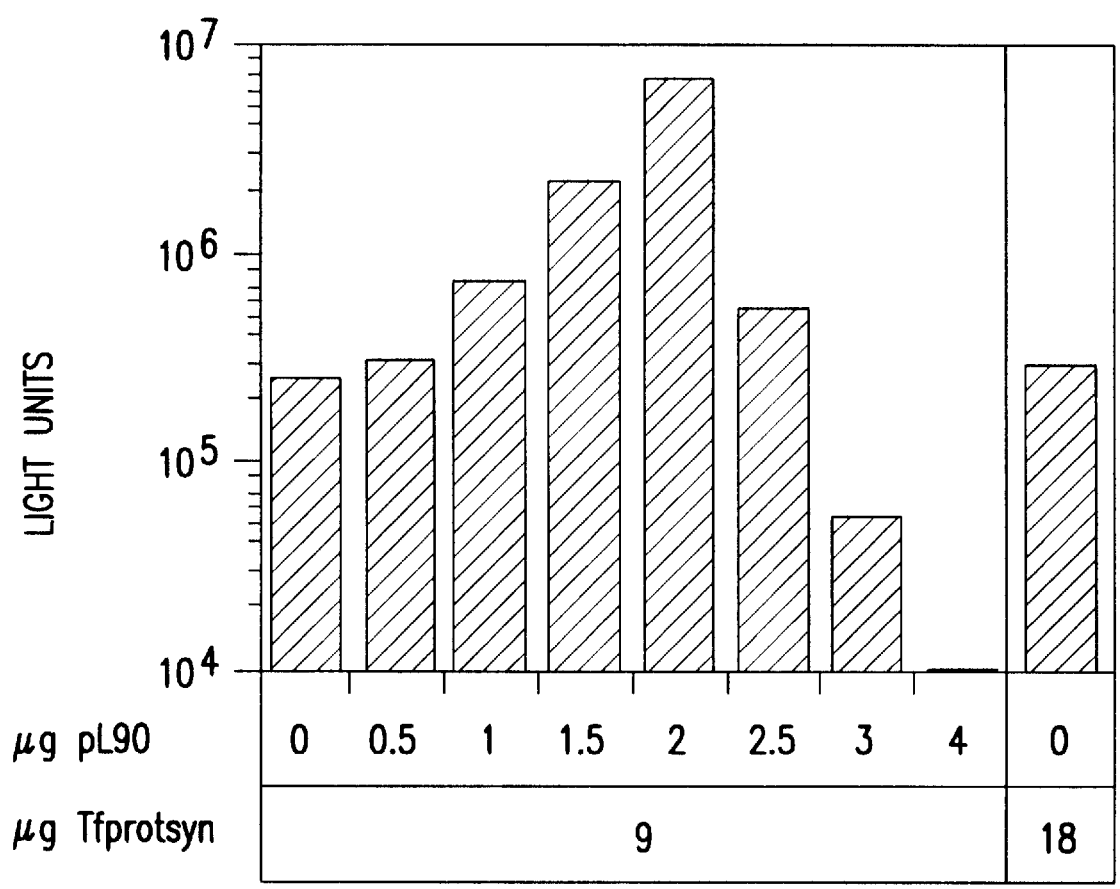
FIG. 5: Improving the efficiency of transferrinfection with conjugates of transferrin and synthetic protamine

Improving the efficiency of transferrinfection with conjugates of transferrin and synthetic protamine by partial replacement with polylysine The complexes formed with 6 μg of pRSVL DNA (the conjugate/DNA ratios are shown in FIG. 4) were mixed with pL90 and used under the same conditions as in the preceding Examples in order to transport DNA into K562 cells (ATCC No. CCL 243). The results of the experiments carried out are shown in FIG. 5; the values for luciferase activity relate to the total extract: if parts of the conjugates containing synthetic protamine are replaced by free polylysine, an increase in DNA expression which may be up to a 20-fold increase can be observed. (For comparison the experiment is shown with the optimum amount determined beforehand; right-hand column in FIG. 5).

Figure 6:
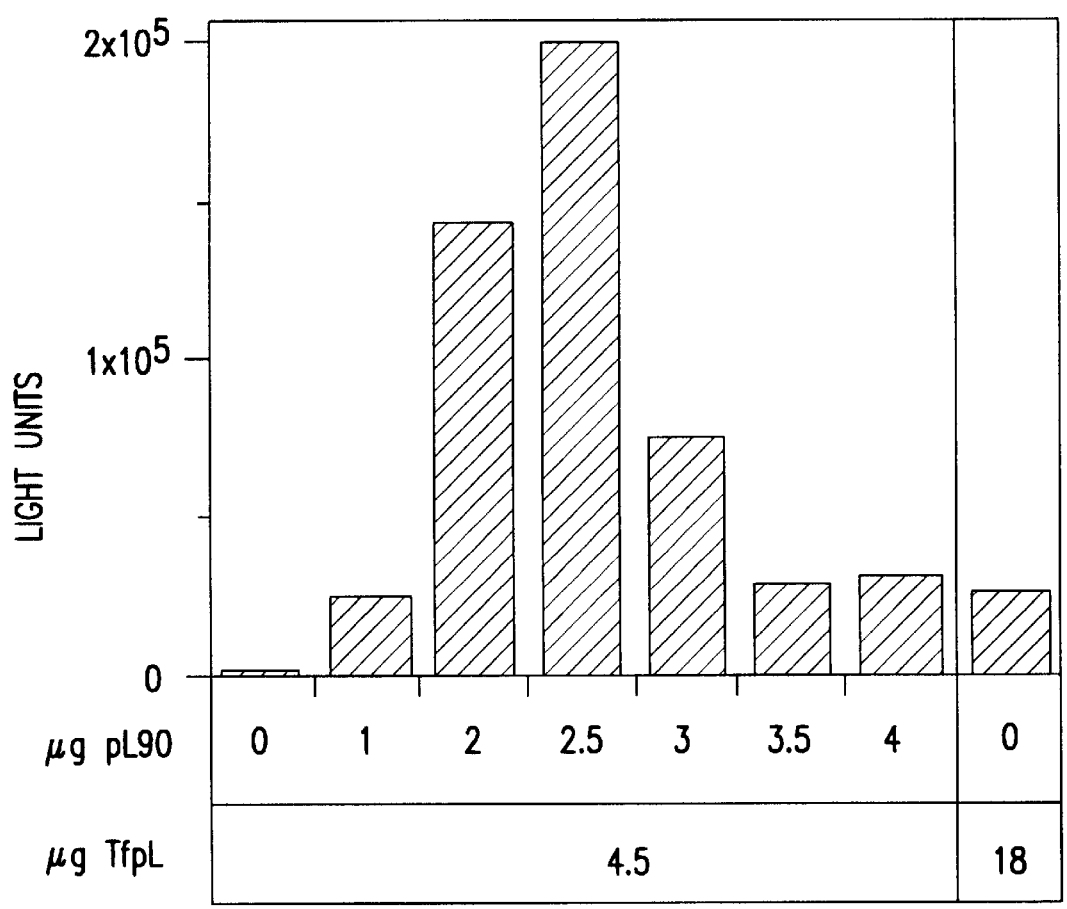
FIG. 6: Increasing the efficiency of transferrinfection depending on the condition of the cells

EXAMPLE 8
Increase in the efficiency of transferrinfection as a function of the state of the cells Within the scope of this Example investigations were made to find out to what extent the degree of improvement in transferrinfection by "diluting" with polylysine depends on the state of the cells. The experiments were basically the same as those in Example 4: starting from 4.5 $\mu$g of TfpL200C, the complexes to be transported into the cells were formed, with the addition of increasing quantities of pL90, but unlike Example 4 the K562 cells were not pretreated with desferrioxamine. The quantity of DNA in the complexes was 6 $\mu$g in all the samples. The cells used for these experiments were investigated for their number of transferrin receptors (Scatchard analysis); it was approximately ⅕ of the cells treated with desferrioxamine. As had been established by means of optimum standard conditions (18 $\mu$g of TfpL200 for 6 $\mu$g of pRSVL DNA), a reduction in DNA expression is found as a consequence of the reduced number of receptors. If, however, in the case of the cells which have not been stimulated with desferrioxamine, ¾ of the transferrin-polylysine conjugates is replaced by polylysine, the DNA expression is increased more than 8-fold. This corresponds to a level which is only 1.8 times lower than in cells having an increased number of receptors as a result of desferrioxamine stimulation. The results of these experiments are shown in FIG. 6. In desferrioxamine-stimulated cells the uptake of DNA mediated by transferrin is not substantially improved by the addition of free polylysine 90.

EXAMPLE 9

Figure 7:
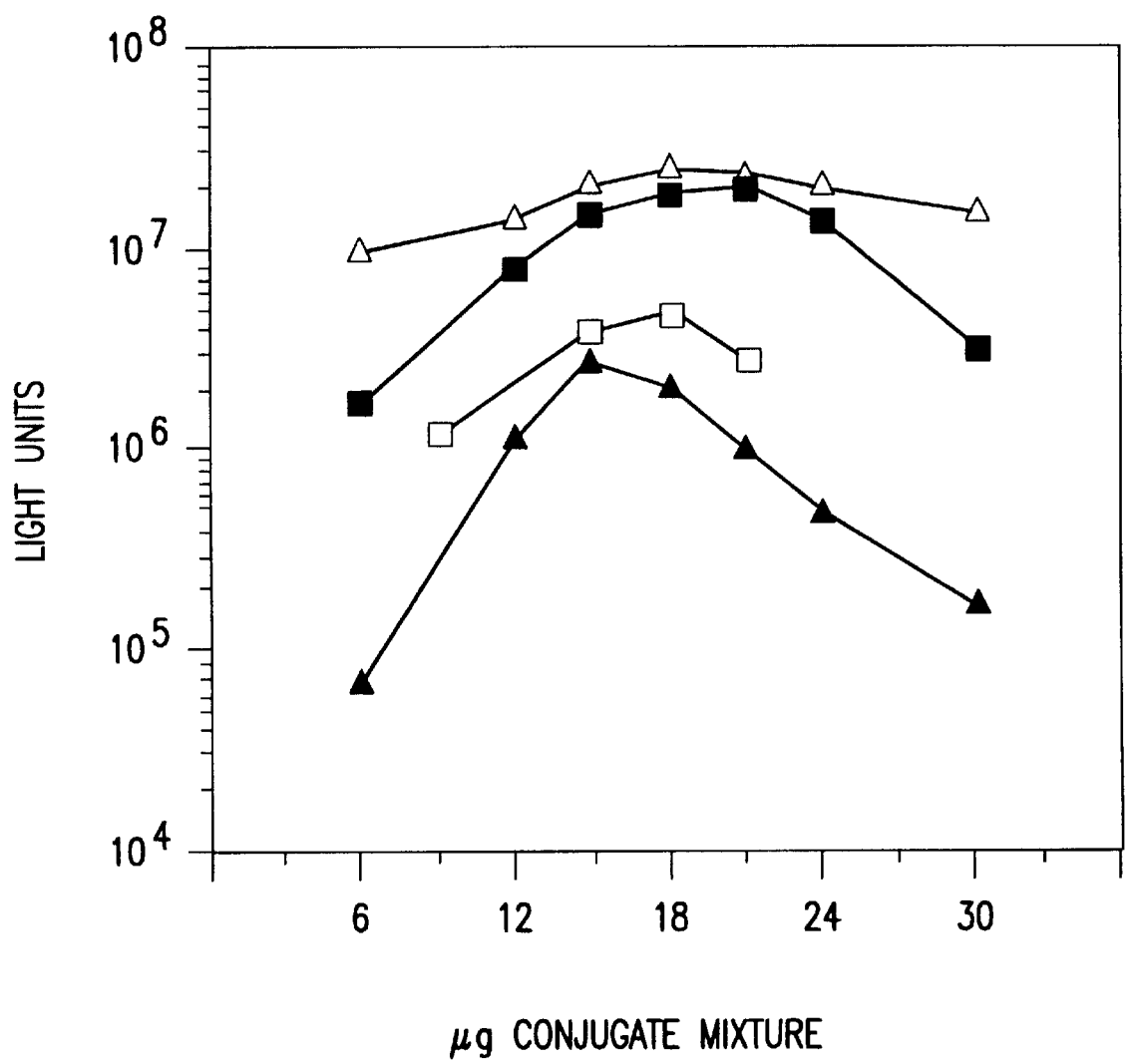
FIG. 7: Influence of non-covalently bound histone H4 on the efficiency of gene transfer

In order to investigate further the effect, observed in Example 4, of the approximately 5-fold increase (Table 1) in gene activity caused by free histone H4, the following experiment was carried out: basic mixtures of TfpL200C conjugates were prepared with 1 (open triangle), 2 (closed square) or 4 (closed triangle) mass equivalents of histone H4 and the optimum quantities for complex forming with a constant quantity of DNA (6 $\mu$g) were determined by a kind of titration for each individual mixture (FIG. 7). The optimum gene activity, achieved by a 4/1 mixture of histone H4/TfpL is comparable with the activity achieved by the conjugate on its own (open square). The investigation of these complexes under the electron microscope showed only a weak condensation of the DNA. Electron microscopy of the H4/TfpL 1/1 complexes showed a stronger but still substantially lower condensation than the pure conjugate-DNA complexes. Surprisingly, however, the increase in transferrinfection when using the 1/1 H4/TfpL mixture was about 7-fold (transfections were carried out under standard conditions as in Example 2; the values for luciferase activity relate to the total extract).

EXAMPLE 10
Transport of DNA in CD4+ cells
a) Preparation of gp120 polylysine 190 conjugates Coupling was carried out (in accordance with the production of the transferrin conjugates) analogously to methods known from the literature, either by introducing disulphide bridges after modification with succinimidyl-pyridyldithiopropionate or by thioether linking after modification with N-hydroxysuccinimide-6-maleimidocaproate (EMCS, Sigma) (Fujiwara et al., 1981).

Disulphide-linked gp120-polylysine 190 conjugates

A solution of 3 mg of recombinant gp120 (prepared by the method described by Lasky et al., 1986) in 50 mM HEPES pH 7.8 was mixed with 7 $\mu$l of 10 mM ethanolic solution of SPDP. After 1 hour at ambient temperature the mixture was filtered over a Sephadex G 25 gel column (eluant 100 mM HEPES buffer pH 7.9) and 2.8 mg (23 nmol) of rgp120 were obtained, modified with 67 nmol of pyridyldithiopropionate residues. A solution of 6.6 nmol polylysine 190, fluorescence-labelled and modified with 23 nmol mercapto groups (after reaction with SPDP, treatment with dithiothreitol and subsequent gel filtration) in 120 $\mu$l of 30 mM sodium acetate was mixed with the modified rgp120 with the exclusion of oxygen and left to stand overnight at ambient temperature. The reaction mixture was adjusted to a content of about 0.6M by the addition of 5M NaCl. The conjugates were isolated by ion exchange chromatography (Mono S, Pharmacia, 50 mM HEPES pH 7.3, salt gradient 0.6M to 3M NaCl); after fractionation and dialysis against 25 mM HEPES pH 7.3, two conjugate fractions A and B were obtained, consisting of 0.33 mg of rgp120 modified with 1.3 nmol polylysine 190 (in the case of fraction A), or 0.34 mg of rgp120 modified with 3.2 nmol of polylysine 190 (fraction B).

Thioether-linked gp120 polylysine 190 conjugates

A solution of 2 mg of recombinant gp120 in 0.45 ml of 100 mM HEPES pH 7.9 was mixed with 17 $\mu$l of a 10 mM solution of EMCS in dimethylformamide. After 1 hour at ambient temperature the mixture was filtered over a Sephadex G 25 gel column (eluant 100 mM HEPES buffer 7.9). The product solution (1.2 ml) was then reacted, with the exclusion of oxygen, with a solution of 9.3 nmol of polylysine 190, fluorescent-labelled and modified with 30 nmol mercapto groups (in 90 $\mu$l 30 mM sodium acetate pH 5.0), and left to stand overnight at ambient temperature. The reaction mixture was adjusted to a content of about 0.6M by the addition of 5M NaCl. The conjugates were isolated by ion exchange chromatography (Mono S, Pharmacia, 50 mM HEPES pH 7.3, salt gradient 0.6M to 3M NaCl); after fractionation and dialysis against 25 mM HEPES pH 7.3, three conjugate fraction A, B and C were obtained, consisting of 0.40 mg of rgp120, modified with 1.9 nmol of polylysine 190 (in the case of fraction A), or 0.25 mg of rgp 120, modified with 2.5 nmol of polylysine 190 (fraction B), or 0.1 mg of rgp 120, modified with 1.6 nmol of polylysine 190 (fraction C).

b) Preparation of gp120-polylysine/DNA complexes

Figure 8:
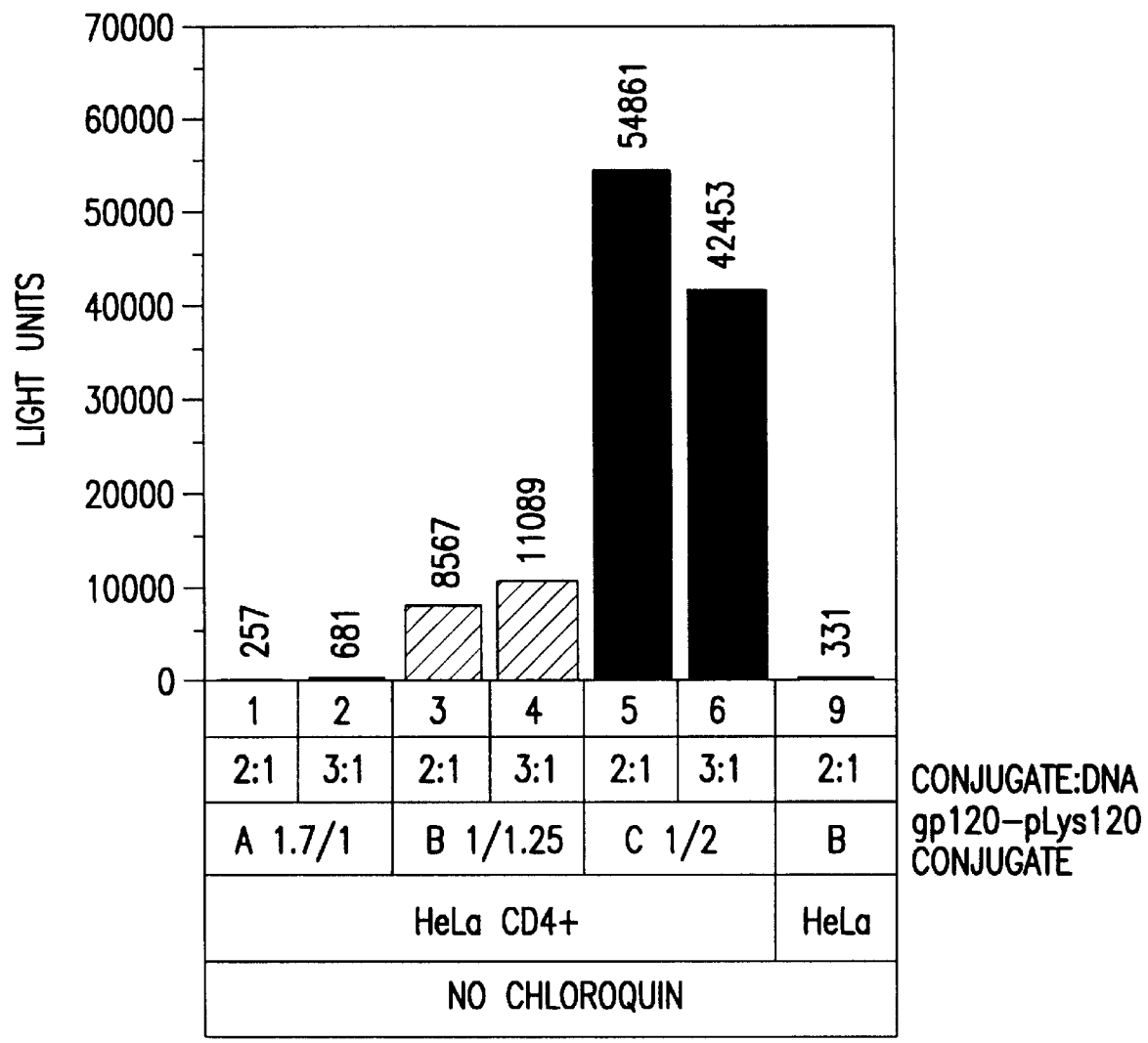
FIG. 8: Gene transfer into CD4 expressing HeLa cells by means of gp120-polylysine conjugates

The complexes were prepared by first diluting 6 $\mu$g of DNA in 330 $\mu$l of HBS at ambient temperature (100 $\mu$g/ml or less). The DNA used was pRSVL plasmid DNA (cf. Example 2). Aliquots of the gp120-pL190 conjugates (the quantities are given in FIG. 8) were diluted in 170 $\mu$l of HBS. The particular conjugate dilution was rapidly added to the DNA dilution, incubated for 30 minutes and then used for transfection.

c) Transfection of CD4+ cells

CD4+ HeLa cells (ATCC No. CCL2; Maddon et al., 1986) were seeded in DEM medium plus 10% FCS (fetal calves' serum) in a quantity of 6×10$^5$ cells per T-25 vial. 18 hours later the cells were washed twice with DEM medium without any serum and incubated in this medium (5 ml) for 5 hours at 37° C. Then the solutions of the gp120-pL/pRSVL complexes were added to the cells. After 4 hours the same volume of DME medium (Dulbecco's modified Eagle's Medium) containing 10% fetal calves' serum was added to each sample. After 24 hours the cells were harvested, extracts were prepared and aliquots of the same protein content (about ⅕ of the total material) were tested for luciferase activity as in the preceding Examples. The values given in FIG. 8 correspond to the luciferase activity of 6×10$^5$ cells. It was found that the activity of the gp120-pL conjugates depends on the ratio of the components, a greater activity being found in the conjugates with a low gp120:polylysine ratio (fraction C, traces 5 and 6) while a very low or no activity was found in the fraction having a high gp120:polylysine ratio (fraction A, traces 1 and 2).

EXAMPLE 11

Figure 9:
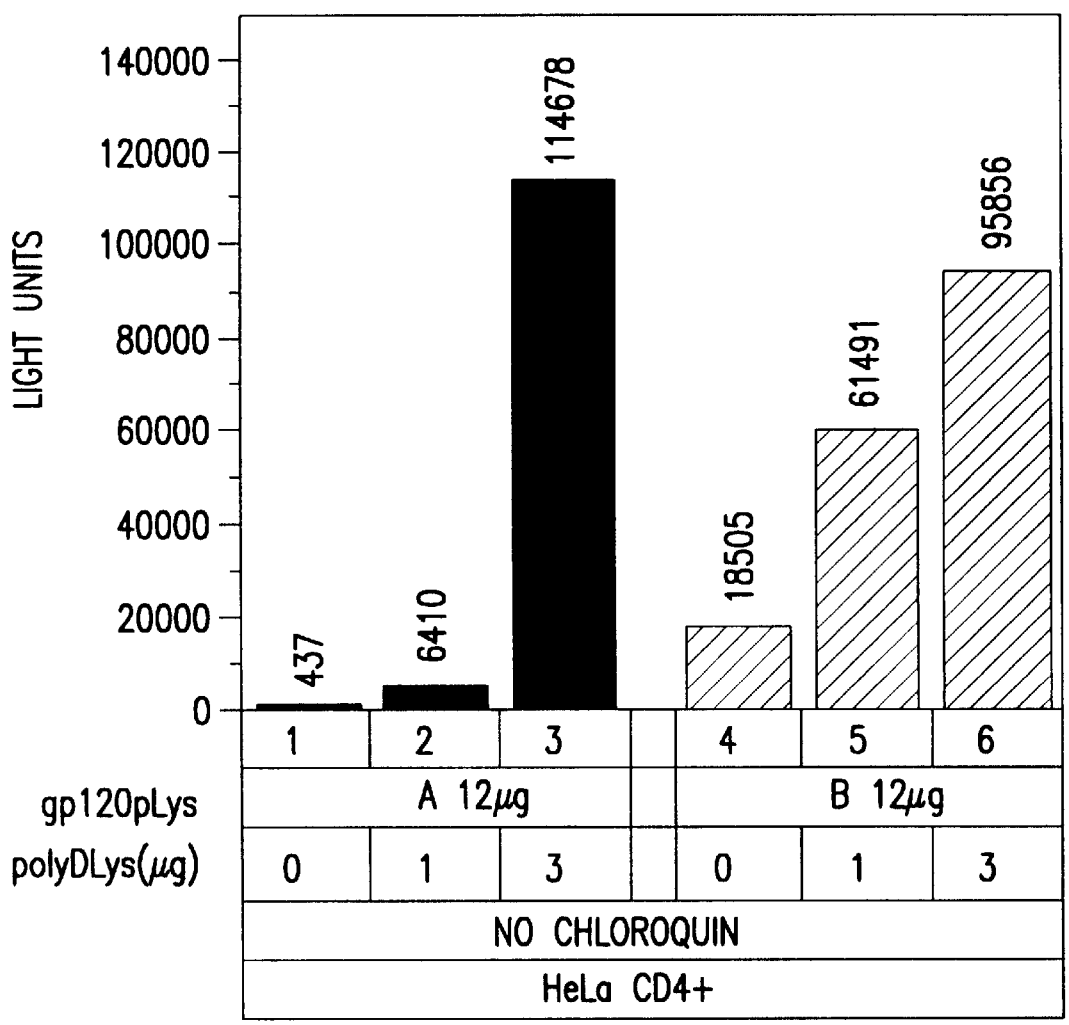
FIG. 9: Increasing the efficiency of gene transfer by means of gp120-polylysine conjugates by the addition of non-covalently bound polylysine

Those gp120-pL conjugates which had demonstrated poor results in transfection in Example 10 (fractions A and B) were investigated to see whether the addition of free polylysine could improve the DNA uptake. 6 μg of DNA and 12 μg of conjugate were used, and 1 or 3 μmg of polylysine 240 were added to the conjugate before the complexing with DNA. As in the results obtained for the transferrin conjugates, a sharp increase in luciferase activity (260-fold or 5.2-fold) was observed (FIG. 9).

EXAMPLE 12

A) Synthesis of N$^\epsilon$-undecyl polylysine (pL200-C11)

The trifluoroacetate salt of polylysine having an average chain length of 200 lysine monomers pL200 was prepared by dissolving 42 mg of pL200 (Hydrobromide salt, Sigma) in 1 ml of 0.5% aqueous trifluoroacetic acid, adding 0.2 ml of 0.3M aqueous N-ethyldiisopropyl-amine/TFA buffer (pH 8) and filtering with 0.5% aqueous trifluoroacetic acid through a Sephadex G25 column (170×14 mm). The product fraction collected (ninhydrin assay) was lyophilized and yielded 44 mg (91%) of pL200 (TFA salt). To a solution of 22 mg (0.48 μmol) of this salt in 3.5 ml of dioxan/water (4/1) was added, at ambient temperature, a solution of 4.1 mg (24 μmol) of undecanal (Sigma) in 50 μl of dioxan (Merck, analytical grade, freshly distilled for use).

Then two batches were added to 12 mg of sodium cyanoborohydride at a 4 hour interval. The reaction mixture was left to stand for 5 days at ambient temperature. Then 200 μl of acetic acid were added and the solvent was distilled off in vacuo. The residue was taken up in 1.2 ml of water/acetic acid/ethanol (65/10/25) and gel-filtered over Sephadex (G25-PD10) with water/acetic acid/ethanol (77/3/20). The product fractions (ninhydrin assay) were lyophilized and yielded 19.7 mg of pL200 (as acetate), modified with about 50–80 undecyl groups per molecule (calculated from the ninhydrin analysis and NMR analysis). The NMR analysis ($^1$H-NMR; D20+15% tetradeuteromethanol) yielded the following values: δ (ppm): 4.15–4.4 (lysine α-H), 3.28 (from deuteromethanol), 2.9–3.1 (lysine $\epsilon$-H and H (C-1, undecyl)), 1.96 (acetate-CH$_3$), 1.1–2.0 (aliphatic CH$_2$ from lysine and undecyl), 0.7–0.9 (undecyl).

B) Cell culture and transfection

Figure 10:
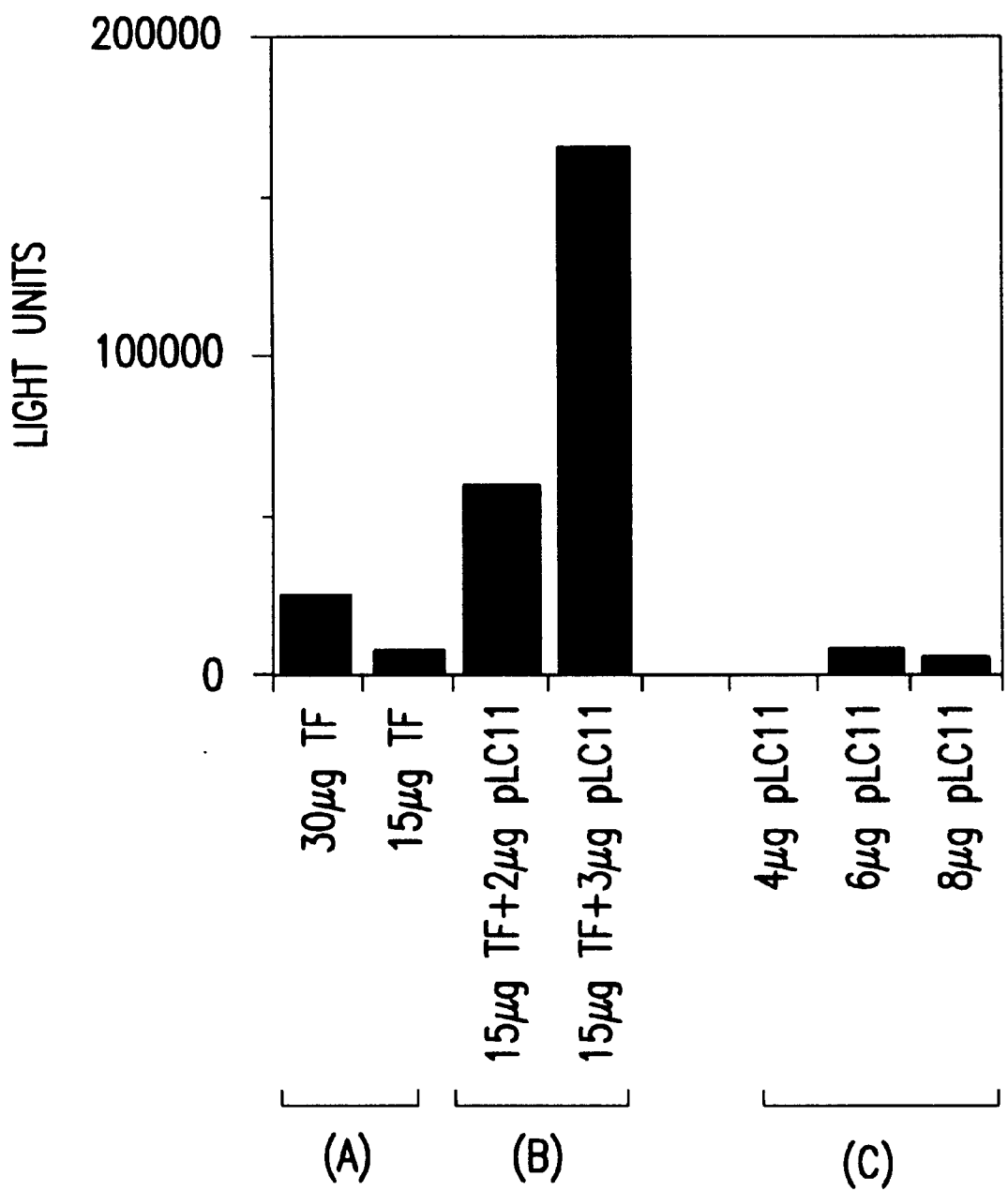
FIG. 10: (panels A–C) Increasing the efficiency of gene transfer by means of transferrin-polylysine-conjugates by the addition of lipophilically modified polylysine

Transfections were carried out with 500,000 HepG2 cells (ATCC No. HB 8065; Knowles et al., 1980) in 5 ml of DMEM plus 10% fetal calves' serum in the presence of 100 μM of chloroquin. (The cells were obtained by trypsinizing them, seeding them with 10 ml of DMEM medium plus 10% fetal calves' serum in vials and leaving them to grow for 24 hours at 37° C. The medium was then replaced by 10 ml of fresh medium, the cells were left to grow for a further 24 hours at 37° C. and the medium was replaced with 5 ml of fresh medium).

a) DNA/conjugate complexes were formed by mixing 330 μl of a solution of 10 μg of pRSVL in HBS with 170 μl of a solution of 15 μg or 30 μg (optimum quantity) of TfpL200 conjugates in HBS. The complexes obtained were used for gene transfer into the cells, as described in the preceding Examples. After 4 hours' incubation at 37° C. the cells were washed and transferred into fresh medium, incubated at 37° C. and harvested 18 hours later for luciferase measurement. Aliquots of the cell extracts, standardized for protein content, were investigated for their luciferase activity; the values, calculated for the total extract, are given in FIG. 10A.

b) DNA conjugate complexes were prepared containing non-covalently bound, modified polycations, by mixing 330 μl of a solution of 10 μg of pRSVL in HBS with 170 μl of a solution containing a mixture of 15 μg of TfpL200 conjugates with varying quantities of pL200-C11 in HBS. The complexes were used under the conditions described above for gene transfer; the luciferase values were also calculated as above and are shown in FIG. 10B (FIG. 10C shows, as a comparison, the values obtained using pL200-C11 on its own).

EXAMPLE 13

A). Preparation of transferrin-ethidium dimer conjugates (Tf-EtD)

A solution of 32 mg (0.4 μmol) of transferrin (human, iron-free, Sigma) in 1 ml of 100 mM sodium acetate buffer pH 5 was gel filtered on a Sephadex G-25 column. The 1.9 ml solution obtained was cooled to 0° C., after which 80 μl of 30 mM sodium acetate buffer pH 5, containing 1.3 mg (6 μmol) of sodium periodate, were added. The mixture was left to stand in an ice bath in the dark for 90 minutes. In order to remove the low molecular products further gel filtration was carried out (Sephadex G-25, 30 mM sodium acetate buffer pH 5), yielding a solution containing about 20 mg (0.25 μmol) of oxidized transferrin (UV absorption at 280 nm and ninhydrin assay; the oxidized form containing aldehydes, unlike the non-modified transferrin, yields a color reaction with anisaldehyde reagent: the sample is added dropwise to a thin layer silica gel plate, immersed in p-anisaldehyde/sulphuric acid/ethanol 1:1:18, dried and heated). The transferrin solution was added to a solution containing 1 mg (1.17 μmol) of ethidium homodimer (5,5'-diazadecamethylene-bis (3,8-diamino-6-phenyl-phenanthridine)dichloride, di HCl, E-1169, Molecular Probes) in 1.2 ml of water. The mixture was kept in the dark, the pH of the solution was adjusted to 7.3 (by the addition of HEPES buffer). Then 2 batches of 1 mg (16 μmol) of sodium cyanoborohydride were each added to 50 μl of water at 4 hour intervals. The reaction mixture was left to stand at ambient temperature and in the dark for 2 days and 3 nights and then gel-filtered (Sephadex G-25 50 mM HEPES pH 7.3). By UV-absorption measurement at 495 nm it was found that, in this step, about 200 μg of non-conjugated ethidium dimer were eliminated together with other low molecular substances. One third of the 4.1 ml solution containing the conjugate was used for purification experiments. The remaining ⅔ were diluted with 0.6M guanidine hydrochloride (buffered to pH 5 with sodium acetate) and applied to a column which separates on the basis of a hydrophobic interaction (Phenyl Sepharose CL-4B Pharmacia, 100×8 mm, about 4.5 ml). A slightly pink solution eluted in the flowthrough, containing 1.5 mg of transferrin. The violet conjugates stayed on the column and were eluted (after washing with 50 ml of 0.6M guanidine hydrochloride) with 0.6M guanidine hydrochloride containing first 2% and 3% of octylglycopyranoside (Sigma). The conjugates were collected as two fractions eluted one after the other (7 ml and 27.5 ml) and dialyzed for 3 days against 2 liters of 200 mM guanidine hydrochloride. Then the fractions were each evaporated down to a volume of 3 ml using a Speedvac (Savant) and dialyzed twice more for 2 days (2 l 25 mM HEPES pH 7.3). This procedure yielded (in spite of the loss caused by the extended dialysis) two fractions of transferrin-ethidium dimer conjugate each containing 2 mg of transferrin (determined both by ninhydrin assay and by Bio-Rad Protein Assay); the two violet colored fractions had 0.42 AU (522 nm) and 0.68 AU (516 nm), respectively. (Since the transferrin-conjugated ethidium dimer had changed its UV absorption properties, the exact content of ethidium dimer in the conjugates could not be determined). Iron was incorporated analogously to Example 1.

Figure 11:
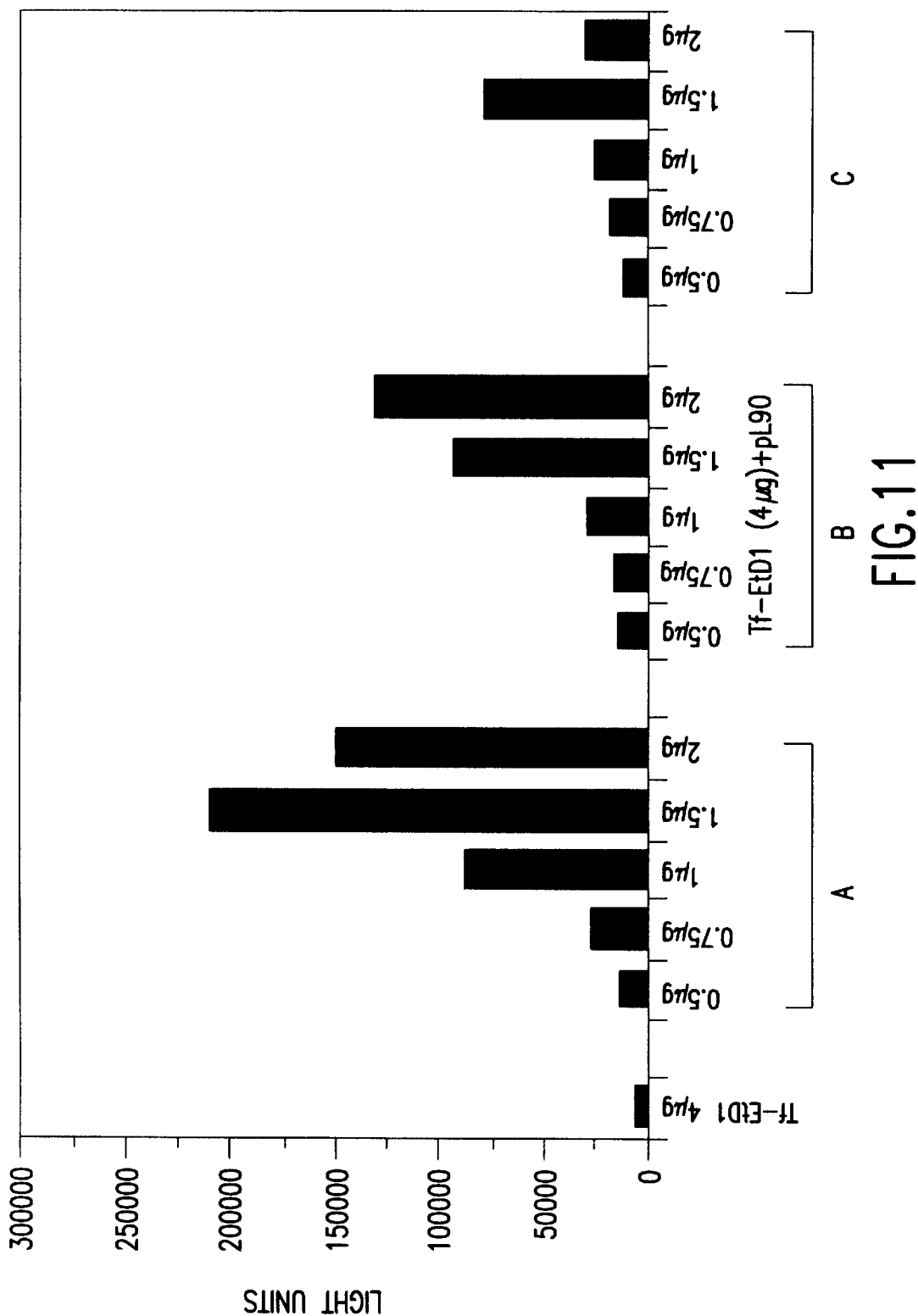
FIG. 11: (panels A–C) Increasing the efficiency of gene transfer by means of transferrin-ethidium dimer conjugates using non-covalently bound polylysine
Figure 11A:
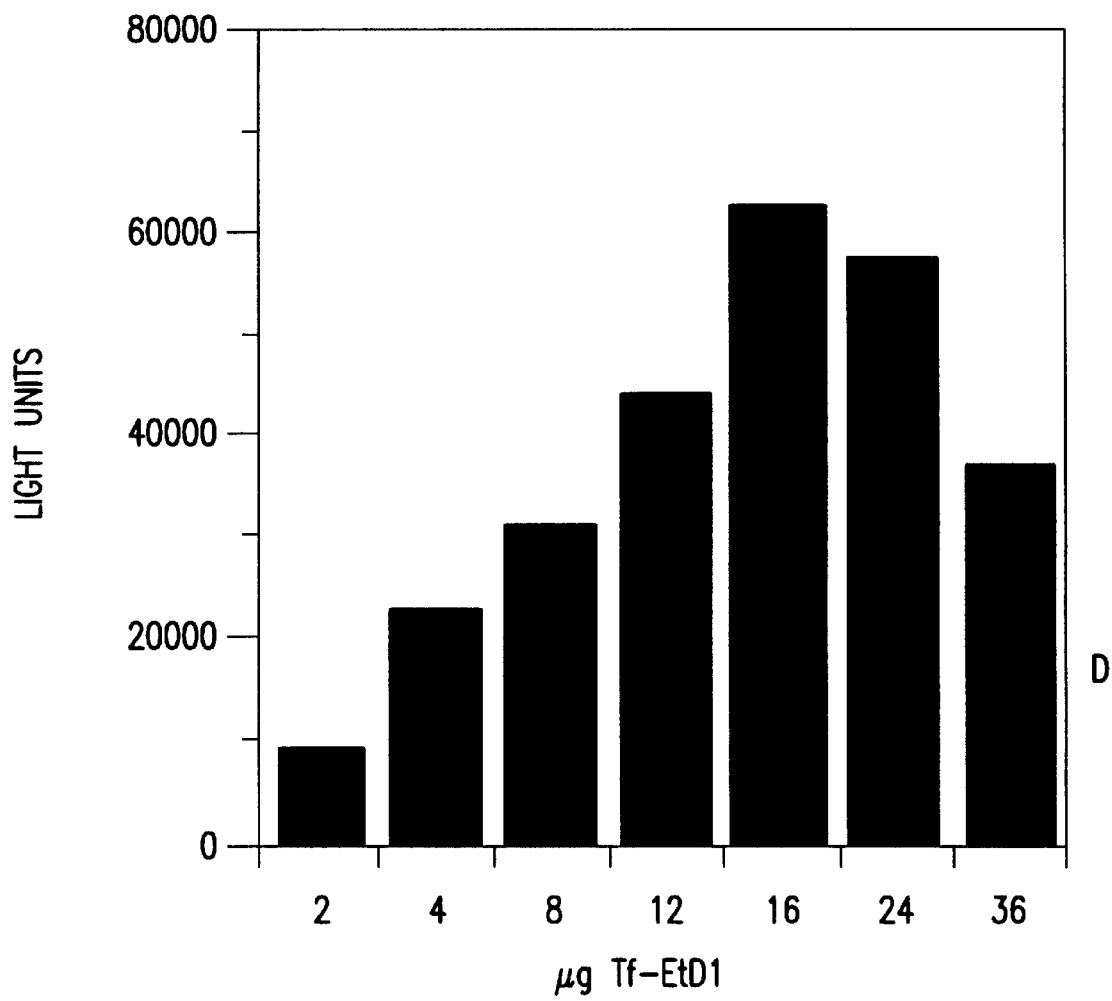

B) Cell culture and transfection a) DNA/conjugate complexes were prepared as described for TfpL conjugates, by mixing 330 µl of solution of 6 µg of pRSVL in HBS with 170 µl of solution of varying quantities of the Tf-EtD conjugates (conjugate fraction 1) in HBS (intercalation) and then adding 170 µl of a solution of varying amounts of pL90 (condensation). The complexes obtained were used for the transfection of 500,000 K562 cells under standard conditions; aliquots of cell extracts, standardized according to their protein content, were investigated for luciferase activity (FIG. 11A). (FIG. 11D shows the results achieved with Tf-EtD conjugates on their own).

b) Complexes containing non-covalently bound polycations were formed by first mixing 170 µl of a solution of 4 µg of Tf-EtD conjugates with 170 µl of a solution of varying amounts of pL90 in HBS and subsequently adding a solution of 170 µl of a solution of 6 µg of pRSVL in HBS (intercalation plus condensation). The transfection and luciferase measurement were carried out as described above (FIG. 11B).

c) Complexes containing non-covalently bound polycations were formed by first mixing 170 µl of a solution of 6 µg of pRSVL in HBS with 170 µl of a solution of varying amounts of pL90 (condensation) and then adding 170 µl of a solution of 4 µg of Tf-EtD conjugates (intercalation). Transfection and luciferase measurement were carried out as described above (FIG. 11C).

EXAMPLE 14 a) Preparation of $N^\epsilon$-lactosylated polylysine (pL-lactose)

To a solution of 16.5 mg (0.44 µmol) of poly(L)lysine with an average chain length of 200 lysine monomers (pL200), acetate salt, in 0.46 ml of 100 mM sodium acetate (pH 5.0) were added 90 mg of lactose (Sigma) which dissolved during 30 minutes stirring at 37° C. While the solution was maintained at this temperature, four batches of 3 mg of sodium cyanoborohydride were added at intervals of about 10 hours. The reaction mixture was left to stand at 37° C. for a further 21 hours. Then 15 µl of acetic acid were added and the reaction mixture was subjected to gel filtration (Sephadex G25-PD10) with 100 mM sodium acetate (pH 5.0). The product fractions (detected by ninhydrin test and stained with anisaldehyde) were dialyzed overnight against 20 mM sodium acetate and then against 0.05% acetic acid. Final lyophilization yielded 26.5 mg of pL200, acetate salt, lactosylated with about 70% of the $N^\epsilon$-lysine-amino groups, as estimated by ninhydrin analysis and NMR analysis.

$^1$H-NMR (D20, 250 MHz, suppression of the solvent signal): δ (ppm): 4.51 (d, J=7.2 Hz; galactose-1H), 4.22–4.34 (lysine α-H), 4.1–4.22 (sugar H), 2.9–4.0 (lysine ε-H and sugar H), 1.91 (acetate-$CH_3$), 1.1–2.0 (aliphatic lysine-$CH_2$).

b) Cell culture and transfection

Figure 12:
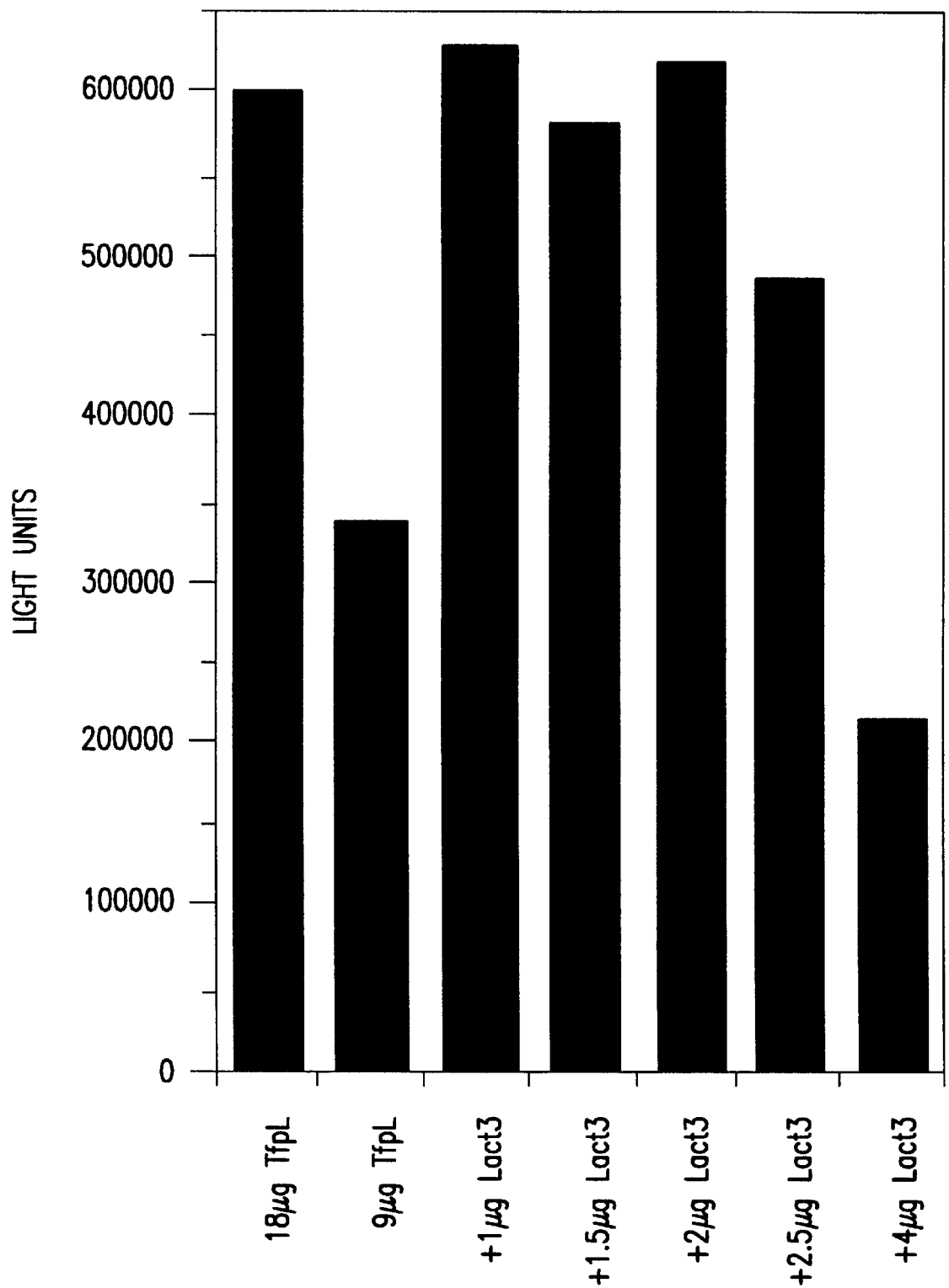
FIG. 12: Effect of lactose-modified polylysine on gene transfer by means of transferrin-polylysine conjugates The present invention is illustrated by means of the Examples which follow.

The transferrinfection was carried out with 500,000 K562 cells and 6 µg of pRSVL DNA and with 18 µg of TfpL, with 9 µg of TfpL and with 9 µg of TfpL with the addition of varying quantities of pL-lactose under standard conditions, as in the preceding Examples, the activities obtained by the luciferase activity are shown in FIG. 12 (the light units given relate to cell extract aliquots (about 15–20% of the total extract), standardized for protein content). It is found that the addition of non-covalently bound lactose-modified polylysine is capable of compensating for the reduction in the efficiency of transferrinfection achieved by using a smaller amount of conjugate.

EXAMPLE 15 a) Preparation of $N^\epsilon$-maltosylated polylysine (pL-maltose)

Exactly the same procedure was used as in Example 14, except that maltose was used to modify polylysine. The following $^1$H-NMR data were obtained: δ (ppm): 5.11 (d, J=3.4 Hz; glucose-1H), 2.95–4.4 (lysine-H and sugar-H), 1.91 (acetate $CH_3$), 1.1–2.0 (aliphatic $CH_2$ of lysine).

b) Influence of pL-maltose on gene transfer

Transferrinfection of 500,000 K562 cells with 6 µg of pRSVL-DNA, carried out as described in Example 14b), yielded, in the case of DNA complexes completely saturated with TfpL (12 µg TfpL190B), 1.01×10$^6$ light units of specific luciferase activity (about 20% of the total sample extract), while semisaturated DNA complexes (6 µg of TfpL190B) yielded 549,000 light units. By adding 2.5 µg of pL-maltose (6 µg TfpL190B+2.5 µg pL-maltose) the efficiency of transfection was increased to 1,215,000 light units.

EXAMPLE 16 a) Preparation of $N^\epsilon$-cellobiose-modified polylysine (pL-cellobiose)

Exactly the same procedure was used as in Example 14 except that cellobiose was used to modify polylysine.

b) Influence of pL-cellobiose on gene transfer

In the transfection of K562 cells under the same conditions as in Example 15b), 1,160,000 light units were obtained by the addition of 2 µg of pL-cellobiose (6 µg TfpL190B+2 µg of pL-cellobiose).

BIBLIOGRAPHY

Böttger, M. et al., (1988), Biochem. Biophys. Acta 950, 221–228

Chattoraj, D. K. et al., (1978) J.Mol.Biol. 121, 327–337

Ciliberto, G. et al., (1985), Cell 41, 531–540

Darnell, J. et al., (1989) in Molecular Cel Biology, page 567, Second edition, edited by W. H. Freeman and Company, New York De Wet et al., (1987), Mol.Cell.Biol. 7, 725–737

Farber, F. E. et al., (1975), Biochim.Biophys.Acta 390, 298–311

Fujiwara et al., (1981), J.Immunol.Meth. 45, 195

Ham, R. G., (1965), Proc.Natl.Sci. U.S.A. 53, 288

Jung et al., (1981), Biochem.Res.Commun. 101, 599

Knowles, B. B. et al., (1980), Science 209, 497–499

Kurachi, K. and Davie, E. W. (1982), Proc.Natl.Acad.Sci.U.S.A. 79, 6461–6464

Laemmli, U.K., (1975), Proc.Nat.Acad.Sci. U.S.A. 72, 4288–4292

Lasky et al., (1986), Science 233, 209–212
Lasky et al., (1987), Cell 50, 975–985
Maddon et al., (1986), Cell 47, 333–348
Maniatis et al., (1982), Molecular Cloning, Cold Spring Harbor
Nygren A. et al., (1988), Proc.Natl.Acad.Sci.U.S.A. 85, 6543–6546
Pelchen-Mattews et al., (1989), EMBO J. 8, 3641–3649
Riordan, J. R. et al., (1989), Science 245, 1066–1073
Tikchonenko T. I. et al., (1988), Gene 63, 321–330
Valerio, D. et al., (1984), Gene 31, 147–153
Wagner, E. et al., (1991), Bioconjugate Chemistry 2, 226–231
Wu, G. Y. and Wu, C. H., (1987), J.Biol.Chem. 262, 4429–4432
Zamecnik et al., (1986), Proc.Natl.Acad.Sci. 83, 4143
Zon, G., (1988), Pharmaceut. Research 5, 539–549

TABLE 1

| μg: | 0 | 1 | 1.5 | 1.75 | 2 | 2.25 | 2.5 | 3 | 4 | 6 | 8 | 10 | 12 | 16 | 32 |
|---|---|---|---|---|---|---|---|---|---|---|---|---|---|---|---|
| pL55 | 21 | 42 | 103 | 67 | 52 | 131 | 149 | 142 | | | | | | | |
| pL90 | 34 | 78 | 166 | 252 | 118 | 50 | 39 | 26 | | | | | | | |
| pL450 | 45 | 102 | | 125 | 176 | 210 | 60 | 26 | | | | | | | |
| p(D)L240 | 21 | 169 | 115 | | 268 | | 344 | 290 | | | | | | | |
| protamine | 56 | 146 | 148 | | 198 | | 175 | 130 | 55 | | | | | | |
| histone H1 | | | | | 96 | | | | | 111 | 112 | 84 | 178 | 133 | 130 | 173 |
| histone H3 | 47 | | | | 91 | | | | 138 | 284 | 153 | 115 | 60 | 44 | 30 |
| histone H4 | 47 | 59 | | | 89 | | | 85 | 122 | 300 | 560 | 211 | 174 | 57 | 1 |
| spermine | 47 | | | | 76 | | | | 85 | | 90 | | | 71 | 63 |
| spermidine | 47 | | | | 76 | | | | 62 | | 59 | | | 56 | 61 |

We claim:

1. A complex for the transfer of nucleic acid into higher eukaryotic cells by endocytosis comprising
   (a) the nucleic acid to be transferred;
   (b) an internalizing factor-bonding factor conjugate complexed to the nucleic acid to be transferred; and
   (c) a non-covalently bound substance having an affinity for nucleic acid, which substance is not a component of said internalizing factor-bonding factor conjugate; wherein
      (i) said internalizing factor is cell type specific for said eukaryotic cells; (ii) said non-covalently bound substance is selected from a group consisting of polycations that are capable of condensing the nucleic acid to be transferred, histones, and HMGI; and (iii) the ability of said complex to internalize and/or achieve expression of said nucleic acid to be transferred is increased compared to the complex containing only the nucleic acid to be transferred and the internalizing factor-bonding factor conjugate.

2. The complex of claim 1, wherein the non-covalently bound substance having an affinity for nucleic acid is made of the same substance as the bonding factor.

3. The complex of claim 1, wherein the internalizing factor is a ligand or a fragment thereof which is absorbed into the cell via receptor-mediated endocytosis.

4. The complex of claim 3, wherein the internalizing factor is transferrin.

5. The complex of claim 1, wherein the internalizing factor is a ligand capable of binding to a surface antigen of the eukaryotic cells.

6. The complex of claim 5, wherein the ligand binds to CD4.

7. The complex of claim 6, wherein the internalizing factor is an anti-CD4 antibody or a viral protein.

8. The complex of claim 1, wherein the bonding factor is a polycationic substance.

9. The complex of claim 8, wherein the bonding factor is a homologous polycation.

10. The complex of claim 9, wherein the bonding factor is polylysine.

11. The complex of claim 1, wherein the bonding factor is an intercalating substance.

12. The complex of claim 1, wherein the substance having an affinity for nucleic acid is modified with a hydrophilic or lipophilic group.

13. The complex of claim 1, wherein the bonding factor is a substance capable of condensing the nucleic acid to be transferred and the substance having an affinity for nucleic acid is a substance which is capable of increasing the internalization or expression of the nucleic acid to be transferred by a mechanism which is different from the mechanism responsible for the condensation of the nucleic acid to be transferred.

14. The complex of claim 13, wherein the bonding factor is polylysine and the non-covalently bound substance having an affinity for nucleic acid is a histone or a mixture of histones.

15. The complex of claim 14, wherein the substance having an affinity for nucleic acid is histone H4.

16. The complex of claim 13, wherein the substance having an affinity for nucleic acid is the non-histone protein HMGI.

17. The complex of claim 13, wherein the internalizing factor is transferrin.

18. A method for the preparation of a complex capable of transferring nucleic acid into higher eukaryotic cells, comprising admixing
   (a) the nucleic acid to be transferred;
   (b) an internalizing factor-bonding factor conjugate; and
   (c) a non-covalently bound substance having an affinity for nucleic acid, which substance is not a component of said internalizing factor-bonding factor conjugate; wherein
      (i) said internalizing factor is cell type specific for said eukaryotic cells; and (ii) said non-covalently bound substance is selected from a group consisting of polycations that are capable of condensing the nucleic acid to be transferred, histones, and HMGI.

19. The method of claim 18, wherein the internalizing factor-bonding factor conjugate is first mixed with the substance having an affinity for nucleic acid and then combined with the nucleic acid to be transferred.

20. The method of claim 18, wherein the nucleic acid to be transferred is first complexed with the internalizing factor-bonding factor conjugate and then mixed with the substance having an affinity for nucleic acid.

21. The method of claim 18, wherein the non-covalently bound substance having an affinity for nucleic acid is made of the same substance as the bonding factor.

22. The method of claim 18, wherein the internalizing factor is a ligand or a fragment thereof which is absorbed into the cell via receptor-mediated endocytosis.

23. The method of claim 22, wherein the internalizing factor is transferrin.

24. The method of claim 18, wherein the internalizing factor is a ligand capable of binding to a surface antigen of the eukaryotic cells.

25. The method according to claim 24, wherein the ligand binds to CD4.

26. The method of claim 25, wherein the internalizing factor is an anti-CD4 antibody or a viral protein.

27. The method of claim 18, wherein the bonding factor is a polycationic substance.

28. The method of claim 27, wherein the bonding factor is a homologous polycation.

29. The method of claim 28, wherein the bonding factor is polylysine.

30. The method of claim 18, wherein the bonding factor is an intercalating substance.

31. A process for transferring nucleic acid into higher eukaryotic cells, comprising bringing said cells into contact with a complex comprising (a) the nucleic acid to be transferred;

(b) an internalizing factor-bonding factor conjugate; and (c) a non-covalently bound substance having an affinity for nucleic acid, which substance is not a component of said internalizing factor-bonding factor conjugate; wherein (i) said internalizing factor is cell type specific for said eukaryotic cells; and (ii) said non-covalently bound substance is selected from a group consisting of polycations that are capable of condensing the nucleic acid to be transferred, histones, and HMGI.

32. The process of claim 31, wherein the non-covalently bound substance having an affinity for nucleic acid is made of the same substance as the bonding factor.

33. The process of claim 31, wherein the internalizing factor is a ligand or a fragment thereof which is absorbed into the cell via receptor-mediated endocytosis.

34. The process of claim 33, wherein the internalizing factor is transferrin.

35. The process of claim 31, wherein the internalizing factor is a ligand capable of binding to a surface antigen of the eukaryotic cells.

36. The process of claim 35, wherein the ligand binds to CD4.

37. The process of claim 36, wherein the internalizing factor is an anti-CD4 antibody or a viral protein.

38. The process of claim 31, wherein the bonding factor is a polycationic substance.

39. The process of claim 38, wherein the bonding factor is a homologous polycation.

40. The process of claim 39, wherein the bonding factor is polylysine.

41. The process of claim 31, wherein the bonding factor is an intercalating substance.

42. The process of claim 31, wherein the substance having an affinity for nucleic acid is modified with a hydrophilic or lipophilic group.

43. The process of claim 31, wherein the bonding factor is a substance capable of condensing the nucleic acid to be transferred and wherein the substance having an affinity for nucleic acid is a substance which is capable of increasing the internalization or expression of the nucleic acid to be transferred by a mechanism which is different from the mechanism responsible for the condensation of the nucleic acid to be transferred.

44. The process of claim 43, wherein the bonding factor is polylysine and the non-covalently bound substance having an affinity for nucleic acid is a histone or mixture of histones.

45. The process of claim 44, wherein the substance having an affinity for nucleic acid is histone H4.

46. The process of claim 43, wherein the substance having an affinity for nucleic acid is the non-histone protein HMGI.

47. The process of claim 31, wherein the cells are exposed to conditions which inhibit the breakdown of nucleic acid in the cell.

48. The process of claim 47, wherein the cells are treated with choloroquin.

49. The process of claim 31, wherein the internalizing factor is transferrin.

50. The process of claim 49, wherein the cell s are exposed to conditions under which the number of transferrin receptors is increased.

51. The process of claim 50, in which the heme concentration in the cells is reduced.

52. The process of claim 51, in which the cells are treated with desferrioxamine.

53. A composition comprising the complex of claim 1, wherein the nucleic acid to be transferred is a therapeutically effective nucleic acid.

54. The composition of claim 53, wherein the therapeutically effective nucleic acid is effective in gene therapy.

55. The composition of claim 53, wherein the therapeutically effective nucleic acid comprises an antisense oligonucleotide.

56. The composition of claim 53, wherein the therapeutically effective nucleic acid comprises a ribozyme or gene coding therefor.

57. The composition of claim 53, wherein the therapeutically effective nucleic acid is a gene construct comprising a sequence coding for an RNA molecule which specifically inhibits a cell function.

* * * * *